US010138293B2

(12) United States Patent
Klein et al.

(10) Patent No.: US 10,138,293 B2
(45) Date of Patent: *Nov. 27, 2018

(54) BIVALENT, BISPECIFIC ANTIBODIES

(75) Inventors: Christian Klein, Iffeldorf (DE); Wolfgang Schaefer, Mannheim (DE)

(73) Assignee: HOFFMANN-LA ROCHE, INC., Nutley, NJ (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/362,000

(22) Filed: Jan. 31, 2012

(65) Prior Publication Data

US 2012/0225071 A1 Sep. 6, 2012

Related U.S. Application Data

(63) Continuation of application No. 12/332,486, filed on Dec. 11, 2008, now abandoned.

(30) Foreign Application Priority Data

Dec. 21, 2007 (EP) .................................... 07024864

(51) Int. Cl.
C07K 16/00 (2006.01)
C07K 16/22 (2006.01)
C07K 16/28 (2006.01)
C07K 16/46 (2006.01)

(52) U.S. Cl.
CPC .............. *C07K 16/00* (2013.01); *C07K 16/22* (2013.01); *C07K 16/2863* (2013.01); *C07K 16/468* (2013.01); *C07K 2317/21* (2013.01); *C07K 2317/31* (2013.01); *C07K 2319/00* (2013.01)

(58) Field of Classification Search
CPC ....... A61K 39/395; C12P 21/00; C12N 15/63; C12N 15/13; C07K 16/18; C07K 16/00; C07K 16/22; C07K 16/468; C07K 16/2863

See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,677,425 A | 10/1997 | Bodmer et al. | |
| 5,731,168 A | 3/1998 | Carter et al. | |
| 5,747,654 A | 5/1998 | Pastan et al. | |
| 5,798,229 A | 8/1998 | Strittmatter et al. | |
| 5,821,333 A | 10/1998 | Carter et al. | |
| 5,959,083 A | 9/1999 | Bosslet et al. | |
| 6,166,185 A | 12/2000 | Davis et al. | |
| 6,239,259 B1 | 5/2001 | Davis et al. | |
| 6,511,663 B1 | 1/2003 | King et al. | |
| 6,558,672 B1 | 5/2003 | Pastan et al. | |
| 6,602,684 B1 | 8/2003 | Umana et al. | |
| 6,897,044 B1 | 5/2005 | Braslawsky et al. | |
| 6,946,292 B2 | 9/2005 | Kanda et al. | |
| 6,982,321 B2 | 1/2006 | Winter | |
| 7,129,330 B1 | 10/2006 | Little et al. | |
| 7,183,076 B2 | 2/2007 | Arathoon et al. | |
| 7,276,585 B2 | 10/2007 | Lazar et al. | |
| 7,317,091 B2 | 1/2008 | Lazar et al. | |
| 7,642,228 B2 | 1/2010 | Carter et al. | |
| 7,651,688 B2 | 1/2010 | Hanai et al. | |
| 7,666,622 B2 | 2/2010 | Sharma et al. | |
| 7,695,936 B2 | 4/2010 | Carter et al. | |
| 7,919,257 B2 | 5/2011 | Hoogenboom et al. | |
| 7,942,042 B2 | 5/2011 | Kawakita et al. | |
| 7,951,917 B1 | 5/2011 | Arathoon et al. | |
| 8,188,231 B2 | 5/2012 | Lazar et al. | |
| 8,216,805 B2 | 7/2012 | Carter et al. | |
| 8,227,577 B2* | 7/2012 | Klein et al. ................. | 530/387.3 |
| 8,242,247 B2* | 8/2012 | Klein et al. ................. | 530/387.1 |
| 8,268,314 B2* | 9/2012 | Baehner ................. | C07K 16/22 424/136.1 |
| 8,304,713 B2 | 11/2012 | Pradel | |
| 8,309,300 B2 | 11/2012 | Jununtula et al. | |
| 8,642,745 B2 | 2/2014 | Arathoon et al. | |
| 8,765,412 B2 | 7/2014 | Matsumoto | |
| 8,796,424 B2 | 8/2014 | Croasdale et al. | |
| 8,945,552 B2* | 2/2015 | Baehner ................. | C07K 16/22 424/136.1 |
| 9,150,639 B2 | 10/2015 | Yamasaki et al. | |
| 9,241,994 B2 | 1/2016 | Igawa | |
| 9,605,084 B2 | 3/2017 | Moore et al. | |
| 9,890,204 B2 | 2/2018 | Brinkmann et al. | |
| 9,982,036 B2 | 5/2018 | Bossenmaier et al. | |
| 2002/0062010 A1 | 5/2002 | Arathoon et al. | |
| 2002/0155537 A1 | 10/2002 | Carter et al. | |
| 2003/0099974 A1 | 5/2003 | Lillie et al. | |
| 2003/0124129 A1 | 7/2003 | Oliner | |

(Continued)

FOREIGN PATENT DOCUMENTS

CN 1173878 A 2/1998
CN 1176659 A 3/1998

(Continued)

OTHER PUBLICATIONS

Merchant, et al, 1998, Nature Biotech. 16: 677-681.*
(Chilean Office Action in Corres. Chilean App 3781-2008 dated Jan. 11, 2012).
Simon et al., "Antibody Domain Mutants Demonstrate Autonomy of the Antigen Binding Site" The EMBO Journal 9(4):1051-1056 (1990).
Muller, K.M. et al., FEBS Letters 422:259-264 ( 1998).
Zuo et al., Protein Engineering 13(5):361-387 ( 2000).
Carter, P., Journal of Immunol. Meth. 248:7-15 ( 2001).
(Translation of Jap Off Act in Corres Jap Appl 2010538441 dated Aug. 14, 2012).

(Continued)

*Primary Examiner* — Prema M Mertz
(74) *Attorney, Agent, or Firm* — Morrison & Foerster LLP

(57) ABSTRACT

The present invention relates to nucleic acids which encode the heavy chains and light chains of a novel domain exchanged, bivalent, bispecific antibody, and vectors comprising the same.

12 Claims, 12 Drawing Sheets

Specification includes a Sequence Listing.

(56) References Cited

U.S. PATENT DOCUMENTS

| | | |
|---|---|---|
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0220388 A1 | 11/2004 | Metens et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0152894 A1 | 7/2005 | Krummen et al. |
| 2005/0163782 A1 | 7/2005 | Glaser et al. |
| 2005/0249722 A1 | 11/2005 | Beliard et al. |
| 2006/0063921 A1 | 3/2006 | Moulder et al. |
| 2006/0122370 A1 | 6/2006 | Oliner et al. |
| 2006/0134709 A1 | 6/2006 | Stavenhagen et al. |
| 2006/0160184 A1 | 7/2006 | Mattheus Hoogenboom et al. |
| 2006/0280747 A1 | 12/2006 | Fuh et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0269369 A1 | 11/2007 | Gegg et al. |
| 2007/0274985 A1 | 11/2007 | Dubel et al. |
| 2007/0274998 A1 | 11/2007 | Uktu |
| 2008/0063641 A1 | 3/2008 | Huang et al. |
| 2008/0187954 A1 | 8/2008 | Kallmeier et al. |
| 2009/0023811 A1 | 1/2009 | Biadatti et al. |
| 2009/0155275 A1 | 6/2009 | Wu et al. |
| 2009/0162360 A1 | 6/2009 | Klein et al. |
| 2009/0175851 A1 | 7/2009 | Klein |
| 2009/0194692 A1 | 9/2009 | Kobaru |
| 2009/0232811 A1 | 9/2009 | Klein |
| 2010/0015133 A1 | 1/2010 | Igawa et al. |
| 2010/0081796 A1 | 4/2010 | Brinkman et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256340 A1 | 10/2010 | Brinkmann et al. |
| 2010/0286374 A1 | 11/2010 | Kannan et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0149879 A1 | 6/2012 | Brinkmann et al. |
| 2012/0164726 A1 | 6/2012 | Klein et al. |
| 2012/0177637 A1 | 7/2012 | Hoogenboom et al. |
| 2012/0184718 A1 | 7/2012 | Bruenker et al. |
| 2012/0237506 A1 | 9/2012 | Bossenmaier et al. |
| 2012/0237507 A1 | 9/2012 | Bossenmaier et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0112914 A1 | 4/2014 | Nezu et al. |
| 2014/0154254 A1 | 6/2014 | Kannan et al. |
| 2014/0199294 A1 | 7/2014 | Mimoto et al. |
| 2014/0322756 A1 | 10/2014 | Arathoon et al. |
| 2014/0370019 A1 | 12/2014 | Bruenker et al. |
| 2014/0370020 A1 | 12/2014 | Kuramochi et al. |
| 2015/0166670 A1 | 6/2015 | Castoldi et al. |
| 2015/0274845 A1 | 10/2015 | Bruenker et al. |
| 2015/0344570 A1 | 12/2015 | Igawa et al. |
| 2016/0168259 A1 | 1/2016 | Igawa |
| 2016/0039937 A1 | 2/2016 | Yamasaki et al. |
| 2016/0075785 A1 | 3/2016 | Ast et al. |
| 2016/0238600 A1 | 4/2016 | Hoogenboom et al. |
| 2016/0130347 A1 | 5/2016 | Bruenker et al. |
| 2016/0208019 A1 | 7/2016 | Bacac et al. |
| 2016/0222132 A1 | 8/2016 | Keyt et al. |
| 2017/0029529 A1 | 2/2017 | Croasdale et al. |
| 2017/0037121 A1 | 2/2017 | Schlothauer |
| 2017/0037153 A1 | 2/2017 | Skolaut et al. |
| 2017/0044246 A1 | 2/2017 | Schlothauer |
| 2017/0096485 A1 | 4/2017 | Bacac et al. |
| 2017/0096495 A1 | 4/2017 | Bacac et al. |
| 2017/0114135 A1 | 4/2017 | Codarri-Deak et al. |
| 2017/0114141 A1 | 4/2017 | Amann et al. |
| 2017/0114146 A1 | 4/2017 | Klein et al. |
| 2017/0129962 A1 | 5/2017 | Regula et al. |
| 2017/0145116 A1 | 5/2017 | Regula et al. |
| 2017/0174786 A1 | 6/2017 | Bacac et al. |
| 2017/0190783 A1 | 7/2017 | Bacac et al. |
| 2017/0247467 A1 | 8/2017 | Amann et al. |
| 2017/0253670 A1 | 9/2017 | Klein et al. |
| 2017/0306018 A1 | 10/2017 | Vu et al. |
| 2017/0306036 A1 | 10/2017 | Vu et al. |
| 2017/0349669 A1 | 12/2017 | Sabine et al. |
| 2018/0037633 A1 | 2/2018 | Bossenmaier et al. |

FOREIGN PATENT DOCUMENTS

| | | |
|---|---|---|
| CN | 12302039 A | 10/1999 |
| CN | 1603345 | 4/2005 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 B1 | 3/1989 |
| EP | 0 307 434 B2 | 3/1989 |
| EP | 1 870 458 A1 | 12/2007 |
| EP | 1 870 459 A1 | 12/2007 |
| EP | 1870459 | 12/2007 |
| EP | 1 925 319 A1 | 5/2008 |
| EP | 2 050 764 A1 | 4/2009 |
| EP | 2 443 154 B1 | 4/2012 |
| EP | 2 554 669 A1 | 2/2013 |
| EP | 2 647 707 A1 | 10/2013 |
| EP | 2 728 002 A1 | 5/2014 |
| EP | 2 787 078 A1 | 10/2014 |
| EP | 2 940 135 A1 | 10/2014 |
| JP | 2008-531049 A | 8/2008 |
| JP | 2011-506510 A | 3/2011 |
| JP | 2012-525149 A | 10/2012 |
| JP | 2013-539461 A | 10/2013 |
| JP | 2015-502373 A | 1/2015 |
| RU | 2005/124281 A | 1/2006 |
| RU | 2295537 C2 | 3/2007 |
| WO | 1993/06217 | 4/1993 |
| WO | WO-1993/10819 A1 | 6/1993 |
| WO | WO-94/09131 A1 | 4/1994 |
| WO | WO-94/10202 A1 | 5/1994 |
| WO | WO-94/29350 A2 | 12/1994 |
| WO | WO-94/29350 A3 | 12/1994 |
| WO | WO-95/09917 A1 | 4/1995 |
| WO | 1996/27011 | 9/1996 |
| WO | WO-96/27612 A1 | 9/1996 |
| WO | WO-97/01580 A1 | 1/1997 |
| WO | WO-97/014719 A1 | 4/1997 |
| WO | WO-97/028267 A1 | 8/1997 |
| WO | WO-97/028267 C1 | 8/1997 |
| WO | WO-98/45331 A2 | 10/1998 |
| WO | WO-98/45331 A3 | 10/1998 |
| WO | WO-98/45332 A2 | 10/1998 |
| WO | WO-98/45332 A3 | 10/1998 |
| WO | WO-98/50431 A2 | 11/1998 |
| WO | 1999/37791 | 7/1999 |
| WO | WO-99/54342 A1 | 10/1999 |
| WO | WO-99/66951 A2 | 12/1999 |
| WO | WO-99/66951 A3 | 12/1999 |
| WO | WO-99/66951 C1 | 12/1999 |
| WO | WO-00/05265 A2 | 2/2000 |
| WO | WO-00/35956 A1 | 6/2000 |
| WO | WO-00/61739 A1 | 10/2000 |
| WO | WO-01/77342 A1 | 10/2001 |
| WO | WO-01/90192 A2 | 11/2001 |
| WO | WO-02/02781 A1 | 1/2002 |
| WO | WO-02/33073 A1 | 4/2002 |
| WO | WO-02/096948 A2 | 11/2002 |
| WO | WO-03/030833 A2 | 4/2003 |
| WO | WO-03/030833 A3 | 4/2003 |
| WO | WO-03/035835 A2 | 5/2003 |
| WO | WO-03/035835 A3 | 5/2003 |

(56) References Cited

FOREIGN PATENT DOCUMENTS

| | | |
|---|---|---|
| WO | WO-03/055993 A1 | 7/2003 |
| WO | WO-03/057134 A2 | 7/2003 |
| WO | WO-03/057134 A3 | 7/2003 |
| WO | WO-03/097105 A1 | 11/2003 |
| WO | WO-03/106501 A1 | 12/2003 |
| WO | WO-2004/003019 A2 | 1/2004 |
| WO | WO-2004/003019 A3 | 1/2004 |
| WO | WO-2004/032961 A1 | 4/2004 |
| WO | WO-2004/058298 A1 | 7/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO-2004/106375 A1 | 12/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/051422 A1 | 6/2005 |
| WO | WO-2005/063816 A2 | 7/2005 |
| WO | WO-2005/063816 A3 | 7/2005 |
| WO | WO-2005/092925 A2 | 10/2005 |
| WO | WO-2005/092925 A3 | 10/2005 |
| WO | WO-2006/020258 A2 | 2/2006 |
| WO | WO-2006/020258 A3 | 2/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/091209 A2 | 8/2006 |
| WO | WO-2006/091209 A3 | 8/2006 |
| WO | 2006/093794 | 9/2006 |
| WO | WO 2006/093794 * | 9/2006 |
| WO | WO-2010/108127 A1 | 9/2006 |
| WO | WO-2006/103100 A2 | 10/2006 |
| WO | WO-2006/103100 A3 | 10/2006 |
| WO | WO-2006/106905 A1 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2006/132352 A1 | 12/2006 |
| WO | WO-2007/024715 A2 | 3/2007 |
| WO | WO-2007/031875 A2 | 3/2007 |
| WO | WO-2007/031875 A3 | 3/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/146959 A2 | 12/2007 |
| WO | WO-2007/146959 A3 | 12/2007 |
| WO | WO-2007/147901 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/022349 A2 | 2/2008 |
| WO | WO-2008/022349 A3 | 2/2008 |
| WO | WO-2008/027236 A2 | 3/2008 |
| WO | WO-2008/027236 A3 | 3/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/032782 A2 | 3/2009 |
| WO | WO-2009/032782 A3 | 3/2009 |
| WO | 09/080251 | 7/2009 |
| WO | 2009/080254 | 7/2009 |
| WO | WO-2009/080252 A1 | 7/2009 |
| WO | WO-2009/080253 A1 | 7/2009 |
| WO | WO-2009/089004 A1 | 7/2009 |
| WO | WO-2009/126944 A1 | 10/2009 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/065882 A1 | 6/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/028952 A1 | 3/2011 |
| WO | WO-2011/034605 A2 | 3/2011 |
| WO | WO-2011/034605 A3 | 3/2011 |
| WO | WO-2011/090762 A1 | 7/2011 |
| WO | WO-2011/097054 A1 | 7/2011 |
| WO | WO-2011/118739 A1 | 9/2011 |
| WO | WO-2011/143545 A1 | 11/2011 |
| WO | WO-2012/023053 A2 | 2/2012 |
| WO | WO-2012/023053 A2 | 2/2012 |
| WO | WO-2012/025525 A1 | 3/2012 |
| WO | WO-2012/025530 A1 | 3/2012 |
| WO | WO-2012/058768 A1 | 5/2012 |
| WO | WO-2012/073985 A1 | 6/2012 |
| WO | WO-2012/075037 A1 | 6/2012 |
| WO | WO-2012/116927 A1 | 9/2012 |
| WO | WO-2012/131555 A2 | 10/2012 |
| WO | WO-2012/131555 A3 | 10/2012 |
| WO | WO-2012/143379 A1 | 10/2012 |
| WO | WO-2013/002362 A1 | 1/2013 |
| WO | WO-2013/012733 A1 | 1/2013 |
| WO | WO-2013/026833 A1 | 2/2013 |
| WO | WO-2013/065708 A1 | 5/2013 |
| WO | WO-2013/092001 A1 | 6/2013 |
| WO | WO-2013/096291 A2 | 6/2013 |
| WO | WO-2013/096291 A3 | 6/2013 |
| WO | WO-2013/150043 A1 | 10/2013 |
| WO | WO-2013/157953 A1 | 10/2013 |
| WO | WO-2013/174873 A1 | 11/2013 |
| WO | WO-2014/049003 A1 | 4/2014 |
| WO | WO-2014/081955 A1 | 5/2014 |

(56) References Cited

FOREIGN PATENT DOCUMENTS

| WO | WO-2014/82179 A1 | 6/2014 |
|---|---|---|
| WO | WO-2014/104165 A1 | 7/2014 |
| WO | WO-2015/101588 A1 | 7/2015 |
| WO | WO-2016/016299 A1 | 2/2016 |
| WO | WO-2016/055432 A2 | 4/2016 |
| WO | WO-2016/055432 A3 | 4/2016 |
| WO | WO-2017/055385 A1 | 4/2017 |
| WO | WO-2017/055392 A1 | 4/2017 |
| WO | WO-2017/055393 A1 | 4/2017 |

OTHER PUBLICATIONS

Schaefer, W. et al., "Immunoglobulin domain crossover as a generic approach for the production of bispecific IgG antibodies" Proceedings of the National Academy of Sciences 108(27):11187-11192 (Jul. 5, 2011).
Grote, M et al., Methods Molecular Biology 901:247-263 ( 2012).
(Chilean Office Act in Corres Chilean App 03781-2008 dated Aug. 17, 2012).
Coloma et al., Nature Biotech. 15:159-163 ( 1997).
(Translation of Korean Office Action in Corres. Appl. 2010-7013760 dated Jan. 31, 2012).
Atwell et al., Journal of Molecular Biology 270:26-35 ( 1997).
Xie et al., Journal of Immunological Methods 296:95-101 ( 2005).
Merchant et al., Nature Biotech. 16:677-681 ( 1998).
Ridgway et al., Protein Eng. 9:617-621 ( 1996).
Morrison et al., Journal of Immunology 160:2802-2808 ( 1998).
Morrison et al., Nature Biotech. 15( Suppl 159-163) ( 1997,).
Schoonjans et al., Journal of Immunology 165:7050-7057 ( 2000).
Chan et al., Molecular Immunology 41:527-538 ( 2004).
Morrison, Nature Biotech. 25:1233-1234 ( 2007).
(International Search Report for EP07024864.6 dated Mar. 14, 2008).
Coloma et al., Nature Biotechnology 15:159-163 ( 1997).
Aggarwal et al., "Fibroblast Activation Protein Peptide Substrates Identified from Human Collagen I Derived Gelatin Cleavage Sites," Biochemistry 47(3):1076-1086, (Jan. 22, 2008).
Anonymous. "Production in Yeasts of Stable Antibody Fragments," Expert Opinion on Therapeutic Patents 7(2):179-183, (1997).
Ausubel et al., Current Protocols in Molecular Biology, Greene Publishing and Wiley Interscience: New York, New York, (Table of Contents Only), (1987).
Avgeris et al., "Kallikrein-related Peptidase Genes as Promising Biomarkers for Prognosis and Monitoring of Human Malignancies," Biol. Chem. 391(5):505-511, (May 2010).
Bao et al., "HER2-mediated Upregulation of MMP-1 is Involved in Gastric Cancer Cell Invasion," Arch Biochem Biophys 499(1-2):49-55, (Jul. 2010).
Barnes et al., "Advanced in Animal Cell Recombinant Protein Production: GS-NSO Expression System," Cytotechnology 32 (2):109-23, (Feb. 2000).
Barnes et al., "Characterization of the Stability of Recombinant Protein Production in the GS-NSO Expression System," Biotechnol Bioeng. 73(4):261-70, (May 2001).
Bera, T.K. et al., "A Bivalent Disulfide-stabilized Fv with Improved Antigen Binding to erbB2," J. Mol. Biol. 281(3):475-483, (Aug. 21, 1998).
Boado, R.J. et al., "IgG-single chain Fv fusion protein therapeutic for Alzheimer's disease: Expression in CHO cells and pharmacokinetics and brain delivery in the rhesus monkey," Biotechnology and Bioengineering 105(3):627-635, (Feb. 15, 2010).
Boerner et al., "Production of Antigen—Specific Human Monoclonal Antibodies From In Vitro-Primed Human Splenocytes," J. Immunol. 147(1):86-95, (Jul. 1991).
Borgström, P. et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," Cancer Research 56:4032-4039, (1996).
Briggs et al., "Cystatin E/M suppresses legumain activity and invasion of human melanoma," BMC Cancer 10(17):1-13, (Jan. 2010).
Brinkmann, "Disulfide-stabilized Fv fragments," Chapter 14 In 2 in Antibody Engineering, Kontermaan et al. eds., vol. 2, Springer-Verlag, Berlin Heidelberg, Germany, pp. 181-189, (Apr. 30, 2010).
Brinkmann et al., "A recombinant immunotoxin containing a disulfide-stabilized Fv fragment," PNAS 90(16):7538-7542, (1993).
Brorson et al., "Mutational Analysis of Avidity and Fine Specificity of Anti-Levan Antibodies," J. Immunol. 163:6694-6701 (1994).
Brüggemann et al., "Comparison of the effector funtions of human immunoglobulins using a matched set of chimeric antibodies" J Exp Med. 166(5):1351-61 (Nov. 1987).
Brüggemann et al., "Designer Mice: The Production of Human Antibody Repertoires in Transgenic Animals" Year in Immuno. 7:33-40, (1993).
Brummell et al., "Probing the combining site of an anti-carbohydrate antibody by saturation-mutagenesis: role of the heavy-chain CDR3 residues," Biochemistry 32(4):1180-1187 (1993).
Brunhouse et al., "Isotypes of IgG: comparison of the primary structures of three pairs of isotypes which differ in their ability to activate complement" Mol Immunol. 16(11): 907-917 (Nov. 1979).
Burgess et al. "Possible dissociation of the heparin-binding and mitogenic activities of heparin-binding (acidic fibroblast growth factor-1 from its receptor-binding activities by site-directed mutagenesis of a single lysine residue," Journal of Cell Biology 111:2129-2138, (Nov. 1990).
Burks et al., "In vitro scanning saturation mutagenesis of an antibody binding pocket," PNAS 94(2):412-417 (1997).
Burton et al., "The Clq Receptor Site on Immunoglobulin G." Nature 288(5789): 338-344 (Nov. 27, 1980).
Caron et al. "Engineered humanized dimeric forms of IgG are more effective antibodies," J. Exp. Med. 176(4):1191-1195, (Oct. 1, 1992).
Carro et al., "Serum insulin-like growth factor I regulates brain amyloid-β levels," Nature Medicine 8(12):1390-1397, (2002, e-pub. Nov. 4, 2002).
Carter et al., "Humanization of an Anti-P185$^{HER2}$ Antibody for Human Cancer Therapy," Proc Natl Acad Sci USA. 89(10): 4285-4289 (May 1992).
Chernaia, "[Cathepsin L from human brain tumor. Purification and contents]." Ukr Biokhim Zh. 70(5):97-103, (Sep.-Oct. 1998). (English Translation of Abstract.) (Article in Russian).
Chitnis et al., "The type 1 insulin-like growth factor receptor pathway," Clin. Cancer Res. 14(20):6364-6370, (Oct. 16, 2008).
Chung et al., "Development of a novel albumin-binding prodrug that is cleaved by urokinase-type-plasminogen activator (uPA)," Bioorg Med Chem Lett. 16(19):5157-5163 (Oct. 1, 2006).
Cohen et al., "Nonchromosomal antibiotic resistance in bacteria: Genetic transformation of Escherichia coli by R-factor DNA," Proc. Natl. Acad. Sci. USA 69(8):2110-2114 (Aug. 1972).
Cole et al., "The EBV-hybridoma technique and its application to human lung cancer," Monoclonal Antibodies and Cancer Therapy, New York: Alan R. Liss, Inc. pp. 77-96 (1985).
Coleman, "Effects of amino acid sequence changes on antibody-antigen interactions," Research in Immunol. 145(1):33-38, (1994).
Cordingley et al., "Substrate requirements of human rhinovirus 3C protease for peptide cleavage in vitro," J. Biol. Chem. 265(16):9062-9065, (1990).
Cortesio et al. (Mar. 10, 2008). "Calpain 2 and PTP1B function in a novel pathway with Src to regulate invadopodia dynamics and breast cancer cell invasion," J. Cell Biol. 180(5):957-971.
Coxon et al., "Combined treatment of angiopoietin and VEGF pathway antagonists enhances antitumor activity in preclinical models of colon carcinoma," 99th AACR Annual Meeting, Abstract #1113, (Apr. 2008).
Crawford et al., "Matrix metalloproteinase-7 is expressed by pancreatic cancer precursors and regulates acinar-to-ductal metaplasia in exocrine pancreas," J. Clin. Invest. 109(11):1437-1444, (Jun. 2002).
Cudic et al., "Extracellular proteases as targets for drug development," Curr. Protein Pept Sci 10(4):297-307, (Aug. 2009).

(56) References Cited

OTHER PUBLICATIONS

Cullen et al., "Granzymes in cancer and immunity," *Cell Death Differ* 17(4):616-623, (Apr. 2010).
Davies et al., "Expression of GnTIII in a recombinant anti-CD20 CHO production cell line: Expression of antibodies with altered glycoforms leads to an increase in ADCC through higher affinity for FcγRIII," *Biotechnol. Bioeng.* 74:288-294, (2001).
Deyev, "Multivalency: the hallmark of antibodies used for optimization of tumor targeting by design," *Bioessays* 30(9):904-918, (2008).
Donaldson et al., "Design and development of masked therapeutic antibodies to limit off-target effects: Application to anti-EGFR antibodies," *Cancer Biology & Therapy* 8(22):2145-2150, (Nov. 15, 2009).
Dufner et al., "Harnessing phage and ribosome display for antibody optimization," *Trends Biotechol.* 24(11):523-29 (2006).
Durocher et al., "High-level and high-throughput recombinant protein production by transient transfection of suspension-growing human 293-EBNA1 cells," *Nucleic Acids Research* 30(2 e9):nine pages, (2002).
Edelman et al., "The covalent structure of an entire γG immunoglobulin molecule," *Proc. Natl. Acad. Sci. USA* 63:78-85, (1969).
Fischer et al., "Bispecific antibodies: Molecules that enable novel therapeutic strategies," *Pathobiology* 74:3-14, (2007).
Flatman et al., "Process analytics for purification of monoclonal antibodies," *J. Chromatogr B* 848:79-87, (2007).
Galamb et al., "Inflammation, adenoma and cancer: objective classification of colon biopsy specimens with gene expression signature," *Dis Markers* 25(1):1-16, (2008).
Geisse et al., "Eukaryotic expression systems: A comparison," *Protein Expression and Purification* 8:271-282 (1996).
Gerspach et al., "Target-selective activation of a TNF prodrug by urokinase-type plasminogen activator (uPA) mediated proteolytic processing at the cell surface," *Cancer Immunol. Immunother* 55:1590-1600 (2006).
Gold et al., "A novel bispecific, trivalent antibody construct for targeting pancreatic carcinoma," *Cancer Res.* 68(12):4819-4826, (2008).
Goldenberg et al., "Bi-Specific Antibodies that Bind Specific Target Tissue and Targeted Conjugates," *Derwent Information Ltd.*, 12 pages, (2012).
Graham et al., "A new technique for the assay of infectivity of human adenovirus 5 DNA," *Virology* 52 (2):456-467, (1973).
Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Hartog et al., "The Insulin-like growth factor 1 receptor in cancer: Old focus, new future," *European Journal of Cancer*, Pergamon Press, Oxford, GB, 43(13):1895-1904, (Aug. 23, 2007).
Henry et al., "Clinical implications of fibroblast activation protein in patients with colon cancer," *Clin Cancer Res.* 13(6):1736-1741, (Mar. 15, 2007).
Hezareh et al., "Effector Function Activities of a Panel of Mutants of a Broadly Neutralizing Antibody against Human Immunodeficiency Virus Type 1," *Journal of Virology* 75(24):12161-12168, (Dec. 2001).
Hollander, "Bispecific antibodies for cancer therapy," *Immunotherapy* 1(2):211-222, (Mar. 2009).
Holliger et al., "Engineered antibody fragments and the rise of single domains," *Nat Biotechnol.* 23(9):1126-1136, (Sep. 2005).
Hoogenboom and Winter., "By-passing immunisation. Human antibodies from synthetic repertoires of germline $V_H$ gene segments rearranged in vitro," *J Mol Biol.* 227 (2):381-388, (Sep. 20, 1992).
Hust et al., "Single Chain Fab (scFab) Fragment," *BMC Biotechnology* 7(14):1-15, (Mar. 8, 2007).
Ibragimova et al., "Stability of the β-Sheet of the WW domain: A molecular dynamics simulation study," *Biophysical Journal* 77:2191-2198, (Oct. 1999).

Idusogie et al., "Mapping of the C1q binding site on rituxan, a Chimeric antibody with a human IgG1Fc," *The Journal of Immunology* 164:4178-4184, (2000).
International Search Report dated Dec. 6, 2011, for PCT Patent Application No. PCT/EP2011/064476 filed on Aug. 23, 2011, seven pages. (149.40).
International Search Report dated Dec. 6, 2011, for PCT Patent Application No. PCT/EP2011/064468 filed on Aug. 23, 2011, seven pages. (150.40).
Jakobovits et al., "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6):2551-2555, (Mar. 15, 1993).
Jakobovits et al., "Germ-line Transmission and Expression of a Human-derived Yeast Artificial Chromosome," *Nature* 362:255-258, (Mar. 1993).
Jang et al., "The structural basis for DNA binding by an anti-DNA autoantibody," *Mol. Immunol.* 35(18):1207-1217 (1998).
Jefferis et al., "IgG-Fc-mediated effector functions: molecular definition of interaction sites for effector ligands and the role of glycosylation," *Immunol Rev.* 163:59-76, (1998).
Jendreyko et al., "Simultaneous, Phenotypic Knockout of VEGF-R2 and Tie-2 With an Intradiabody Enhances Antiangiogenic Effects In Vivo," *Therapieoptimierung and Risikostratifizierung*, Scripps Research Institute, 218:143-151, (2006).
Jia et al., "A novel trifunctional IgG-like bispecific antibody to inhibit HIV-1 infection and enhance lysis of HIV by targeting activation of complement," *Virology Journal* 7(142):1-4, (Jun. 29, 2010).
Johnson et al., "Kabat Database and its applications: 30 years after the first variability plot," *Nucleic Acids Research* 28(1):214-218, (2000).
Kabat et al., "Evolutionary and structural influences on light chain constant ($C_L$) region of human and mouse immunoglobulins," *Proc. Natl. Acad. Sci. USA* 72(7):2785-2788, (Jul. 1975).
Kabat et al., *Sequences of Proteins of Immunological Interest* (Table of Contents and Introduction), 5th edition, Bethesda, MD: Public Health Service, NIH, vol. 1, (1991).
Karadag et al., "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278, (Apr. 2006).
Kaufman, "Overview of Vector Design for Mammalian Gene Expression," *Molecular Biotechnology* 16:151-160, (2000).
Kazama et al., "Hepsin, a putative membrane-associated serine protease, activates human factor VII and initiates a pathway of blood coagulation on the cell surface leading to thrombin formation," *JBC* 270:66-72, (1995).
Kim et al., "Inhibition of Vascular Endothelial Growth Factor-Induced Angiogenesis Suppresses Tumour Growth In Vivo," *Nature* 362:841-844, (1993).
Kleinschmidt et al., "Design of a modular immunotoxin connected by polyionic adapter peptides," *J. Mol. Biol.* 327(2):445-452, (Mar. 21, 2003).
Kobayashi et al., "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kobayshi et al. "Tryptophan H33 plays an important role in pyrimidine (6-4) pyrimidone photoproduct binding by a high-affinity antibody," *Protein Engineering* 12(10):879-844 (1999).
Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Lamkanfi et al., "Inflammasomes: guardians of cytosolic sanctity," *Immunol. Rev.* 227(1):95-105, (Jan. 2009).
Lazar et al., "Transforming growth factor α: Mutation of aspartic acid 47 and leucine 48 results in different biological activities," *Molecular and Cellular Biology* 8(3):1247-1252, (Mar. 1988).

(56) References Cited

OTHER PUBLICATIONS

Lee et al., "Using substrate specificity of antiplasmin-cleaving enzyme for fibroblast activation protein inhibitor design," *Biochemistry* 48(23):5149-5158, (Jun. 16, 2009).
Leeman et al., "The Structure, Regulation, and Function of Human Matrix Metalloproteinase-13," *Crit. Rev Biochem Mol. Biol.* 37(3):149-166, (2002).
Lifely et al., "Glycosylation and Biological Activity of CAMPATH-1H Expressed in Different Cell Lines and Grown Under Different Culture Conditions," *Glycobiology* 5(8):813-822, (Dec. 1995).
Liang et al., "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).
Lin et al., "Structure-Function relationships in glucagon: Properties of highly purified des-his-, monoiodo-, and [Des-Asn$^{28}$, Thr$^{29}$](homoserine lacton$^{27}$)-glucagon," *Biochemistry USA* 14:1559-1563, (1975).
Liotta et al., "Metastatic potential correlates with enzymatic degradation of basement membrane collagen," *Nature* 284(5751) 67-68, (Mar. 6, 1980).
Liu et al., "Clinical and imaging diagnosis of primary hepatic lymphoma," *J First Mil Med. Univ*, 25(10):1290-1292, three pages, (2005). (Translation of the Abstract Only.).
Lopez-Otin et al., "The regulatory crosstalk between kinases and proteases in cancer," *Nat. Rev. Cancer* 10(4):278-292, (Apr. 2010).
Love et al., "Recombinant antibodies possessing novel effector functions," *Methods in Enzymology* 178:515-527, (1989).
Lu et al., "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al., "ADAMTS1 and MMP1 proteolytically engage EGF-like ligands in an osteolytic signaling cascade for bone metastasis," *Genes Dev.* 23(16):1882-1894, (Aug. 2009).
Lukas et al., "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).
Lund et al., "Oligosaccharide-protein interactions in IgG can modulate recognition by Fcγ receptors," *FASEB Journal* 9:115-119, (1995).
Makrides, "Components of Vectors for Gene Transfer and Expression in Mammalian Cells," *Protein Expression and Purification* 17:183-202, (1999).
Mamoune et al., "Calpain-2 as a target for limiting prostate cancer invasion," *Cancer Res.* 63(15):4632-4640, (Aug. 2003).
Marks et al., "By-Passing Immunization: Human Antibodies From V-gene Libraries Displayed on Phage," *J Mol Biol.* 222(3):581-597, (Dec. 5, 1991).
Marvin et al., "Recombinant approaches to IgG-like bispecific antibodies," *Acta Pharmacol. Sin.* 26:649-658, (2005).
Marvin et al., "Bispecific antibodies for dual-modality cancer therapy: killing two signaling cascades with one stone," *Curr. Opin. Drug Discov. Devl.* 9:184-193, (2006).
Matrisian. "Cancer biology: extracellular proteinases in malignancy," *Curr. Biol.* 9(20):R776-R778, (Oct. 1999).
Meissner et al., "Transient Gene Expression: Recombinant Protein Production with Suspension-Adapted HEK293-EBNA Cells," *Biotechnology and Bioengineering* 75:197-203, (2001).
Melnyk et al., "Vascular Endothelial Growth Factor Promotes Tumor Dissemination by a Mechanism Distinct from Its Effect on Primary Tumor Growth," *Cancer Research* 56:921-924, (1996).
Michaelson et al., "Anti-tumor activity of stability-engineered IgG-like bispecific antibodies targeting TRAIL-R2 and LTβR," *MAbs* 1(2):128-141, (Mar. 2009, e-pub. Mar. 11, 2009).
Milstein et al., "Hybrid Hybridomas and Their Use in Immunohistochemistry," *Nature* 305: 537-540, (Oct. 6, 1983).

Miller et al., "Design, Construction, and In Vitro Analyses of Multivalent Antibodies," *J. Immunol.* 170:4854-4861, (2003).
Mimura et al., "Role of Oligosaccharide Residues of IgG1-Fc in FcγRIIb Binding," *The Journal of Biological Chemistry* 276(49): 45539-45547, (Dec. 7, 2001).
Minn et al., "Genes that Mediate Breast Cancer Metastasis to Lung," *Nature* 436(7050):518-524, (Jul. 2005).
Morgan et al., "The N-terminal End of the $C_H2$ Domain of Chimeric Human IgG1 anti-HLA-DR is Necessary for C1q, FcγRI and FcγRIII Binding," *Immunology* 86:319-324, (1995).
Morrison et al., "Chimeric Human Antibody Molecules: Mouse Antigen-Binding Domains with Human Constant Region Domains," *Proc. Natl. Acad. Sci. USA* 81(21) :6851-6855, (Nov. 1984).
Morrison. "Success in Specification," *Nature* 368:812-813, (Apr. 1994).
Mukhopadhyay et al., "Matrix metalloproteinase-12 is a therapeutic target for asthma in children and young adults," *J. Allergy Clin Immunol.* 126:70-76, (2010).
Müller et al., "Bispecific Antibodies," Chapter 2 in Handbook of Therapeutic Antibodies, Dübel, S. ed., Wiley-VCH Verlag GmbH & Company KGaA, Weinheim, pp. 345-378, (2007).
Müller et al., "Recombinant Bispecific Antibodies for Cellular Cancer Immunotherapy," *Current Opinion in Molecular Therapeutics* 9:319-326, (2007).
Netzel-Arnett et al., "Sequence Specificities of Human Fibroblast and Neutrophil Collagenases," *J. Biol. Chem.* 266(11):6747-6755, (Apr. 15, 1991).
Netzel-Arnett et al., "Comparative sequence specificities of human 72- and 92-kDa gelatinases (type IV collagenases) and PUMP (matrilysin)," *Biochemistry* 32(25):6427-6432, (Jun. 29, 1993).
Neuberger et al., "A hapten-specific chimaeric IgE antibody with human physiological effector function," *Nature* 314:268-270, (Mar. 21, 1985).
Niwa et al., "IgG subclass-independent improvement of antibody-dependent cellular cytotoxicity by fucose removal from Asn$^{297}$-linked oligosaccharides," *J. Immunol. Methods* 306:151-160, (2005).
Norderhaug et al., "Versatile Vectors for Transient and Stable Expression of Recombinant Antibody Molecules in Mammalian Cells," *Journal of Immunological Methods* 204:77-87, (1997).
Ohno et al., "Antigen-binding specificities of antibodies are primarily determined by seven residues of $V_H$," *Proc. Natl. Acad. Sci. USA* 82(9):2945-2949, (May 1985).
Oliner et al., "Suppression of Angiogenesis and Tumor Growth by Selective Inhibition of Angiopoietin-2," *Cancer Cell* 6:507-516, (2004).
Orcutt, et al., "A modular IgG-scFv bispecific antibody topology," *Protein Engineering, Design & Selection* 23(4):221-228, (Apr. 2010, e-pub. Dec. 17, 2009).
Orlandi et al., "Cloning Immunoglobulin Variable Domains for Expression by the Polymerase Chain Reaction," *Proc. Natl. Acad. Sci. USA* 86:3833-3837, (May 1989).
Pace et al., "How to Measure and Predict the Molar Absorption Coefficient of a Protein," *Protein Science* 4(11): 2411-2423, (Nov. 1995).
Pakula et al., "Genetic analysis of protein stability and function," *Annu. Rev. Genet.* 23:289-310, (1989).
Plückthun et al., "New Protein Engineering Approaches to Multivalent and Bispecific Antibody Fragments," *Immunotechnology* 3:83-105, (1997).
PreScission Protease, GE Healthcare Catalogue No. 27-0843-01, located at www.gelifesciences.com/webapp/wcs/stores/servlet/productById/en/GELifeScience, last visited on Jul. 10, 2013, one page.
Radaev et al., "Recognition of IgG by Fcγ Receptor," *The Journal of Biological Chemistry* 276(19): 16478-16483, (May 11, 2001).
Rajagopal et al., "A Form of Anti-Tac(Fv) Which is Both Single-chain and Disulfide Stabilized: Comparison with its single-chain and Disulfide-stabilized Homologs," *Protein Engineering* 10(12):1453-1459, (1997).
Raju. "Glycosylation Variations with Expression Systems and Their Impact on Biological Activity of Therapeutic Immunoglobulins," *BioProcess International* 1(4): 44-53, (Apr. 2003).

(56) References Cited

OTHER PUBLICATIONS

Rawlings, "A large and accurate collection of peptidase cleavages in the *MEROPS* database," Database (Oxford), pp. 1-14, (2009, e-pub. Nov. 2, 2009).
Reiter et al., "Antitumor activity and pharmacokinetics in mice of a recombinant immunotoxin containing a disulfide-stabilized Fv fragment," *Cancer Research* 54:2714-2718, (1994).
Reiter et al., "Cytotoxic and antitumor activity of a recombinant immunotoxin composed of disulfide-stabilized anti-Tac Fv fragment and truncated *Pseudomonas* exotoxin," *International Journal of Cancer* 58:142-149, (1994).
Reiter et al., "Construction of a functional disulfide-stabilized TCR Fv indicates that antibody and TCR Fv frameworks are very similar in structure," *Immunity* 2:281-287, (1995).
Reiter et al., "Disulfide stabilization of antibody Fv: computer predictions and experimental evaluation," *Protein Engineering* 8:1323-1331, (1995).
Reiter et al., "Engineering antibody Fv fragments for cancer detection and therapy: disulfide-stabilized Fv fragments," *Nature Biotechnology* 14:1239-1245, (1996).
Reiter et al., "Antibody engineering of recombinant Fv immunotoxins for improved targeting of cancer: disulfide-stabilized Fv immunotoxins," *Clin. Cancer Res.* 2(2):245-252, (Feb. 1, 1996).
Riechmann et al., "Reshaping Human Antibodies for Therapy," *Nature* 332:323-327, (Mar. 24, 1988).
Roitt et al., "Immunology," English Translation by McElroy Translation Company, Moscow "Mir" (2000), p. 110-111, eight pages.
Rossi, E.A. et al., "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).
Routier et al., "The Glycosylation Pattern of a Humanized IgGI Antibody (D1.3) Expressed in CHO Cells," *Glycoconjugate Journal* 14:201-207, (1997).
Ruppert et al., "Protease levels in breast, ovary and other gynecological tumor tissues: prognostic importance in breast cancer," *Cancer Detect. Prev.* 21(5):452-459, (1997).
Sambrook et al., *Molecular Cloning: A Laboratory Manual* "The Table of Contents" Cold Spring Harbor, New York: Cold Spring Harbor Laboratory Press, (1989).
Schlaeger, "The Protein Hydrolysate, Primatone RL, is a Cost Effective Multiple Growth Promoter of Mammalian Cell Culture in Serum-containing and Serum-free Media and Displays Antiapoptosis Properties," *Journal of Immunological Methods* 194:191-199, (1996).
Schlaeger et al., "Transient Gene Expression in Mammalian Cells Grown in Serum-free Suspension Culture," *Cytotechnology* 30:71-83, (1999).
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al., "Expression of a bispecific dsFv-dsFv' antibody fragment in *Escherichia coli*" *Protein Engineering* 13(10):725-734, (Oct. 2000).
Schwartz et al., "A superactive insulin: [B10-aspartic acid]insulin(human)," *Proc. Natl. Acad. Sci. USA* 84:6408-6411, (Sep. 1987).
Scott et al., "Biologic protease inhibitors as novel therapeutic agents," *Biochimie* 92(11):1681-1688, (Nov. 2010).
Shen et al., "Single variable domain antibody as a versatile building block for the construction of IgG-like bispecific antibodies," *Journal of Immunological Methods* 318:65-74, (2007).
Shen et al., "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Shields et al., "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (2001).
Shields et al., "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al., "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Simmons et al., "Expression of full-length immunoglobulins in *Escherichia coli*: Rapid and Efficient production of aglycosylated antibodies," *Journal of Immunological Methods* 263:133-147, (2002).
Singer, M. and Berg, P. "Genes and genomes," Moscoer,*MIR* 1(1998) 63-64 (With English Translation.).
Stetler-Stevenson et al., "Progelatinase A activation during tumor cell invasion," *Invasion Metastasis* 14(1-6):259-268, (1994-1995).
Stevenson et al., "A chimeric antibody with dual Fc regions (bisFabFc) prepared by manipulations at the IgG hinge," *Anti-cancer Drug Des.* 3(4):219-230, (Mar. 1989).
Thommesen et al., "Lysine 322 in the human IgG3 $C_H2$ domain is crucial for antibody dependent complement activation," *Molecular Immunology* 37:995-1004, (2000).
Tripathi et al., "Laminin-332 is a substrate for hepsin, a protease associated with prostate cancer progression," *JBC* 283:30576-30584, (2008).
Umaña et al., "Engineered Glycoforms of an Antineuroblastoma IgG1 with Optimized Antibody-Dependent Cellular Cytotoxic Activity," *Nature Biotechnology* 17(2):176-180 (Feb. 1999).
Van Dijk and Van De Winkel., "Human antibodies as next generation therapeutics," *Curr Opin Chem Biol*. 5(4): 368-74, (Aug. 2001).
Van Spriel et al., "Immunotherapeutic perspective for bispecific antibodies," *Immunology Today* 21(8):391-397, (Aug. 2000).
Van'T Veer et al., "Gene expression profiling predicts clinical outcome of breast cancer," *Nature* 415(6871):530-536, (Jan. 2002).
Vazquez-Ortiz et al., "Overexpression of cathepsin F, matrix metalloproteinases 11 and 12 in cervical cancer," *BMC Cancer* 5:68, (Jun. 30, 2005).
Velasco et al., "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).
Veveris-Lowe et al., "Seminal Fluid Characterization for Male Fertility and Prostate Cancer: Kallikrein-Related Serine Proteases and whole Proteome Approaches," *Semin Thromb Hemost*. 33(1):87-99, (2007).
Vijayalakshmi, "Antibody Purification Methods," *Applied Biochemistry and Biotechnology* 75:93-102, (1998).
Walker et al., "Efficient and Rapid Affinity Purification of Proteins Using Recombinant Fusion Proteases," *Bio/Technology* 12:601-605, (1994).
Warren et al., "Regulation of Vascular Endothelial Growth Factor of Human Colon Cancer Tumorigenesis in a Mouse Model of Experimental Liver Metastasis," *J. Clin. Invest.* 95:1789-1797, (1995).
Webber et al., "Preparation and characterization of a disulfide-stabilized Fv fragment of the anti-Tac antibody: comparison with its single-chain analog," *Molecular Immunology* 32:249-258, (1995).
Werner et al., "Appropriate Mammalian Expression Systems for Biopharmaceuticals," *Drug Research* 48(8):870-880, (1998).
Wielockx et al., "Matrilysin (matrix metalloproteinase-7): a new promising drug target in cancer and inflammation?," *Cytokine Growth Factor Rev.* 15(2-3):111-115, (Apr.-Jun. 2004).
Willems et al., "Optimizing expression and purification from cell culture medium of trispecific recombinant antibody derivatives," *Journal of Chromatography B* 786:161-176, (2003).
Woof et al., "Human antibody-FC receptor interactions illuminated by crystal structures," *Nat. Rev. Immunol.* 4:1-11, (2004).
Wright et al., "ADAM28: a potential oncogene involved in asbestos-related lung adenocarcinomas," *Genes Chromosomes Cancer* 49(8):688-698, (Aug. 2010).
Wright and Morrison, "Effect of Glycosylation on Antibody Function: Implications for Genetic Engineering," *Trends in Biotechnology* 15:26-32, (1997).

(56) References Cited

OTHER PUBLICATIONS

Written Opinion of the International Searching Authority dated Dec. 6, 2011, for PCT Patent Application No. PCT/EP2011/064476 filed on Aug. 23, 2011, four pages.
Written Opinion of the International Searching Authority dated Dec. 6, 2011, for PCT Patent Application No. PCT/EP2011/064468 filed on Aug. 23, 2011, four pages.
Wu et al., "Simultaneous Targeting of Multiple Disease Mediators by a Dual-Variable-Domain Immunoglobulin," *Nature Biotechnology* 25(11):1290-1297, (Nov. 2007).
Zeidler et al., "Simultaneous activation of T cells and accessory cells by a new class of intact bispecific antibody results in efficient tumor cell killing," *Journal of Immunology* 163:1246-1252, (1999).
Chinese Office Action dated Mar. 28, 2012, for Chinese Application No. 200880120258.8, 10 pages.
Korean Office Action dated Feb. 24, 2012, for Korean Patent Application No. 20107013773, six pages.
Citations from Israeli Office Action, dated Feb. 29, 2012, in Israeli Patent Application No. 205285, two pages.
Japanese Office Action dated Aug. 14, 2012, for Japanese Patent Application No. 2010-538440, 12 pages.
European Search Report dated Aug. 31, 2009, for European Patent Application No. 09005108.7, six pages.
Taiwanese Search Report for Taiwanese Patent Application No. 099110151, filed on Apr. 1, 2010, Completion of Search Sep. 12, 2012, one page.
International Search Report dated Aug. 5, 2010, for PCT Application No. PCT/EP2010/003559, filed on Jun. 14, 2010, 10 pages.
Dall'Acqua, W. et al. (1998). "Contribution of Domain Interface Residues to the Stability of Antibody CH3 Domain Homodimers", *Biochemistry*, 37:9266-9273.
Dimmock, N.J. et al. (2004). "Valency of antibody binding to virions and its determination by surface plasmon resonance", *Rev. Med. Virol.*, 14:123-135.
McLean, G.R. et al. (2005). "A point mutation in the CH3 domain of human IgG3 inhibits antibody secretion without affecting antigen specificity", *Molecular Immunology*, 42:1111-1119.
Mirny, L. et al. (2001). "Protein Folding Theory: From Lattice to All-Atom Models", *Annu. Rev. Biophys. Biomol. Struct.*, 30-361-96.
Novotný, J. et al. (1985). "Structural invariants of antigen binding: Comparison of immunoglobulin $V_L$-$V_H$ and $V_L$- $V_L$ domain dimmers", *Proc. Natl. Acad. Sci. USA*, 82:4592-4596.
Torres, M. et al. (2005). "Variable-Region-Identical Antibodies Differing in Isotype Demonstrate Differences in Fine Specificity and Idiotype", *The Journal of Immunology*, 174:2132.
Huston, J.S. et al. (1993). "Medical Applications of Single-Chain Antibodies," *Intern. Rev. Immunol.* 10(2-3):195-217.
Russian Office Action dated Apr. 18, 2013, for Russian Patent Application No. 2010 129 539, 3 pages.
Russian Office Action dated Oct. 8, 2014, for Russian Patent Application No. 2012 100 865, 3 pages.
U.S. Appl. No. 14/551,957, filed Nov. 24, 1014 for Castoldi et al.
Stork et al. "A novel tri-functional antibody fusion protein with improved pharmacokinetic properties generated by fusing a bispecific single-chain diabody with an albumin-binding domain from streptococcal protein G," *Protein Eng. Des. Sel.* 20(11):569-576, (Nov. 2007, e-pub. Nov. 3, 2007).
Budtschanow et al. "System of Humoral Immunity Antibodies (Theme 2)," Guidance Manual for General Immunology, Twer (2008) p. 3, English Translation, 3 pages.
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-2002, (2010, e-pub. Feb. 4, 2010).
Greenwood et al. "Structural Motifs Involved in Human IgG Antibody Effector Functions,". *Eur. J. Immunology* 23(5):1098-1104, (May 1993).

Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Pan et al. "Blocking Neuropilin-1 Function Has an Additive Effect with nti-VEGF to Ihibit Tumor Growth," *Cancer Cell* 11:53-67, (Jan. 2007).
Pleass et al. "Identification of Residues in the CH2/CH3 Domain Interface of IgA Essential for Interaction With the Human fcα receptor (FcαR) CD89," *The Journal of Biology Chemistry* 274(33):23508-23514, (Aug. 13, 1999).
Roitt A. et al. "Multispecific Antibodies Comprising Full Length Antibodies and Single Chain Fab Fragments," *Immunology*, English Translation, Moscow:Mir, pp. 388-389, (2000).
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).
Baserga et al. "The IGF-1 Receptor in Cancer Biology," *Int. J. Cancer* 107:873-877, (2003).
Beckman et al. "Antibody Constructs in Cancer Therapy. Protein Engineering Strategies to Imporve Exposure in Solid Tumors," *Cancer* 109(2):170-179, (Jan. 15, 2007, e-pub. Dec. 11, 2006).
Bird et al. "Single-Chain Antigen-Binding Proteins," *Science* 242(4877):423-6, (Oct. 21, 1988).
Bird et al. "Single-Chain Antigen-Binding Proteins," *Science* 244(4903):409, Erratum, (Apr. 28, 1989).
Bostrom et al. (2009). "Variants of the Antibody Herceptin That Interact With HER2 and VEGF at the Antigen Binding Site," *Science* 323:1610-1614.
Brocks et al. "A TNF receptor antagonistic scFv, which is not secreted in mammalian cells, is expressed as a soluble mono- and bivalent scFv derivative in insect cells," *Immunotechnology* 3: 173-184, (1997).
Casset et al. "A peptide mimetic of an anti-CD4 monoclonal," *Biochem and Biophys Res Comm*. 307:198-205, (2003).
Castoldi et al. (2012). "Molecular Characterization of Novel Trispecific ErbB-cMet-IGF1R Antibodies and Their Antigen-Binding Properties," *Prot. Engin. Des. Selection* 25:551-560.
Céspdes et al. "Mouse Models in Oncogeneis and Cancer Therapy," *Clin. Transl. Oncol.* 8(5):318-329 (2006).
Chicheportiche et al."TWEAK, a New Secreted Ligand in the Tumor Necrosis Factor Family That Weakly Induces Apoptosis," *J. Biol. Chem*. 272(51):32401-32410, (1997).
Cuesta et al. (2010). "Multivalent Antibodies: When Design Surpasses Evolution," *Trends Biotech*. 28:355-362.
Dennis."Off by a Whisker," *Nature* 442:739-741, (2006).
Fenn et al., "Crystal Structure of an Anti-Ang2 CrossFab Demonstrates Complete Structural and Functional Integrity of the Variable Domain," PLOS ONE 8(4):e61953 (Apr. 1, 2013).
Fiedler and Skerra. "Purification and Characterisation of His-Tagged Antibody Fragments"; in Kontermann and Dubel (Eds.), *Antibody Engineering*, Springer Lab Manuals, pp. 223-256, (2001).
Fujimori et al. "A Modeling Analysis of Monoclonal Antibody Percolation Through Tumors: A Binding-Site Barrier," *J. Nuc. Med.* 31(7):1191-1198, (Jul. 1990).
Hellings et al., "Interleukin-17 orchestrates the granulocyte influx into airways after allergen inhalation in a mouse model of allergic asthma" *Am J Respir Cell Mol Biol* 28:42-50 (2003).
Huston et al. "Protein Engineering of Antibody Binding Sites: Recovery of Specific Activity in an Anti-Digoxin Single-Chain Fv analogue Produced in *Escherichia coli*," *Proc. Natl. Acad. Sci. U.S.A.* 85(16):5879-5883, (Aug. 1988).
Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).
Johnson et al. "Construction of Single-Chain Fv Derivatives Monoclonal Antibodies and their Production in *Escherichia coli,*" *Methods Enzymol.* 203:88-98, (1991).
Klein et al., "Progress in Overcoming the Chain Association Issue in Bispecific Heterodimeric IgG Antibodies" *mAbs* 4(6):653-663, (2012).

(56) References Cited

OTHER PUBLICATIONS

Komiyama et al. "IL-17 plays an important role in the development of experimental autoimmune encephalomyelitis" *J Immunol* 177:566-573, (2006).
Kotake et al. "IL-17 in synovial fluids from patients with rheumatoid arthritis is a potent stimulator of osteoclastogenesis,"*J. Clin. Invest.* 103:1345-1352, (1999).
Kumar et al. ":Molecular Cloning and Expression of the Fabs of Human Autoantibodies in *Escherichia coli,*" *J. Biol. Chem.* 275(45):35129-35136, (Nov. 10, 2000).
Leitzgen et al. "Assembly of Immunoglobulin Light Chains as a Prerequisite for Secretion," *Journal of Biological Chemistry* 272(5):3117-3123, (1997).
Lodish et al. "Post-Translational Modifications and Quality Control in the Rough ER," Chaper 17, Section 17.6 of *Molecular Cell Biology*, 4th edition, pp. 707-712, (1999).
Lynch et al. "TWEAK Induces Angiogenesis and Proliferation of Endothelial Cells," *J. Biol. Chem.* 274:8455-8459, (1999).
Marsters et al. "Identification of a Ligand for the Death-Domain-Containing Receptor Apo3," *Curr. Biol.* 8:525-528, (1998).
Matusevicius et al. "Interleukin-17 mRNA Expression in Blood and CSF Mononuclear Cells is Augmented in Multiple Sclerosis," *Multiple Sclerosis* 5:101-104, (1999).
Metz et al. "Bispecific Antibody Derivatives With Restricted Binding Functionalities that are Activated by Proteolytic Processing," *Prot. Eng. Des. Sel.* 25:571-580, (2012).
Myatt et al. "Pathogenic Potential of Human Monoclonal Immunoglobulin Light Chains: Relationship of in vitro Aggregation to in vivo Organ Deposition," *Proc. Natl. Acad. Sci. USA* 91:3034-3038, (Apr. 1994).
Paul. (1984). Fundamental Immunolgy, Chapter "Immunoglobulins: Structure and Function," Jeske, D.D. et al.New York, New York, Raven Press, p. 131-165. (1 page translation of 7.9.1 Disculfide Bonds).
Reiter et al. "Stabilization of the Fv Fragments in Recombinant Immunotoxins by Disulfide Bonds Engineered into Conserved Framework Regions," *Biochemistry* 33:5451-5449, (1994).
Reiter et al. "Improved binding and antitumor activity of a recombinant anti-erbB2 immunotoxin by disulfide stabilization of the Fv fragment,"*JBC* 269:18327-18331, (1994).
Reiter et al. "Engineering interchain disulfide bonds into conserved framework regions of Fv fragments: improved biochemical characteristics of recombinant immunotoxins containing disulfide-stabilized Fv," *Protein Eng.* 7(5):697-704, (May 1994).
Rudikoff et al. "Single amino acid substitution altering antigen-binding specificity," *Proc. Natl. Acad. Sci. USA* 79: 1979-1983, (1982).
Rudnick et al. "Affinity and Avidity in Antibody-Based Tumor Targeting," *Cancer Biotherapy & Radiopharmaceuticals* 24(2):155-162 (2009).
Schlatter et al. "On the Optimal Ratio of Heavy to Light Chain Genes for Efficient Recombinant Antibody Production by CHO Cells," *Biotechnol. Prog.* 21 :122-133, (2005).
Schmiedl et al. "Effects of Unpaired Cysteines on Yield, Solubility and Activity of Different Recombinant Antibody Constructs Expressed in *E. coli*" *Journal of Immunological Methods* 242: 101-114, (2000).
Smith-Gill et al. "Contributions of Immunoglpbulin Heavy and Light Chains 5o Antibody Specificity for Lysozyme and Two Haptens," *J. Immunol.* 139(12):4135-4144, (Dec. 15, 1987).
Song al."Light Chain of Natural Antibody Plays a Dominant Role in Protein Antigen Binding,"*Biochem. Biophys. Res. Comm.* 268(2):390-394, (Feb. 16, 2000).
Talmadge et al. "Murine Models to Evaluate Novel and Conventional Therapeutic Strategies for Cancer," *Am. J. Pathol* 170(3):793-804, (Mar. 2007).
Terpe. "Overview of Tag Protein Fusions: From Molecular and Biochemical Fundamentals to Commercial Systems," *Appl Microbiol Biotechnol* 60:523-533, (2003).

Thurber et al. "Antibody Tumor Penetration: Transport Opposed by Systemic and Antigen-Mediated Clearance," *Adv. Drug Deliv. Rev.* 60(12):1421-1434, (Sep. 2008, E-Pub. Apr. 24, 2008).
Ueki et al. "Expression of Hepatocyte Growth Factor and its Receptor c-met Proto-Oncogene in Hepatocellular Carcinoma," *Hepatology* 25(4):862-866, (1997).
Voskoglou-Nomikos et al. "Clinical Predictive Value of the in Vitro Cell Line, Human Xenograft, and Mouse Allograft Preclinical Cancer Models," *Clin. Can. Res.* 9:4227-4239, (Sep. 15, 2003).
Wallash et al. "Heregulin-Dependent Regulation of HER2/neu Oncogenic Signaling by Heterodimerization With HER3," *Embo J.* 14(17):4267-4275, (1985).
Ward et al. "Binding Activities of a Repertoire of Single Immunoglobulin Variable Domains Secreted From *Escherichia coli,* "*Nature 341*:544-546, (Oct. 12, 1989).
Ziolkowska et al. "High Levels of IL-17 in Rheumatoid Arthritis Patients: IL-15 Triggers In Vitro IL-17 Production Via Cyclosporin A-Sensitive Mechanism," *J. Immunol.* 164:2832-2838, (2000).
International Search Report dated Jul. 29, 2013, for PCT Patent Application No. PCT/EP2013/060529, filed on May 22, 2013, seven pages.
International Search Report dated Sep. 9, 2015, for PCT Application No. PCT/EP2015/057165, filed on Apr. 1, 2015, 5 pages.
Written Opinion of the International Searching Authority dated Jul. 29, 2013, for PCT Patent Application No. PCT/EP2013/060529, filed on May 22, 2013, seven pages.
Written Opinion dated Sep. 9, 2015, for PCT Application No. PCT/EP2015/057165, filed on Apr. 1, 2015, 7 pages.
Alt, M et al. (Jul. 2, 1999). "Novel Tetravalent and Bispecific IgG-Like Antibody Molecules Combining Single-chain Diabodies With the Immunoglobulin γ1 Fc or CH3 Region," *FEBS Lett.* 454(1-2):90-94.
Lewis, M.L. et al. (Feb. 1, 2014, e-pub. Jan. 26, 2014). "Generation of Bispecific IgG Antibodies by Structure-Based Design on an Orthogonal Fab Interface," *Nature Biotechnology* 32(2):191-198.
Nagaoka, M. et al. (2003). "Single Amino Acid Substitution in the Mouse IgG1 Fc Region Induces Drastic Enhancement of the Affinity to Protein A," *Protein Engineering* 16(4):243-245.
Patentee's Submission of Jun. 11, 2012, for European Patent No. 1 957 533, filed on Oct. 23, 2006, Reply to Communication Pursuant to Article 94(3) EPC dated Dec. 2, 2011, 7 pages.
Reyes, A.E. et al. (2008). "Pharmacokinetics of a Novel One Armed Antibody to C-Met in Mice, Rats and Monkeys," Genentech, Inc., *Amer. Assn. Pharm. Sci.* 10:S1.
Surati, M. et al. (2011). "Role of MetMAb (OA-5D5) in c-MET Active Lung Malignancies," *Expert Opin. Biol. Ther.* 11(12):1655-1662.
International Search Report, dated Sep. 29, 2015 for PCT/EP2015/067369, filed on Jul. 29, 2015, 5 pages.
Written Opinion of the International Searching Authority dated Sep. 29, 2015, for PCT Patent Application No. PCT/EP2015/067369 filed on Jul. 29, 2015, 6 pages.
Bacac, M. et al. (2016, e-pub. Feb. 9, 2016). "A Novel Carcinoembryonic Antigen T-Cell Bispecific Antibody (CEA TCB) for the Treatment of Solid Tumors," *Clin. Cancer Res.* 22(13):3286-3297.
Croasdale, R. et al. (2012, e-pub. Mar. 21, 2012) "Development of Tetravalent IgG1 Dual Targeting IGF-1 R-EGFR Antibodies With Potent Tumor Inhibition," *Archives of Biochemistry and Biophysics* 526:206-218.
Cruse, J.M., et al., 2nd ed., CRC Press (2003) p. 37, 316-317.
Klein, C. et al. (2016). "The Use of CrossMAb Technology for the Generation of Bi- and Multispecific Antibodies," *MABS*. 8(6):1010-1020.
Olafsen, T. et al. (1999). "Complement-Mediated Lysis of Cultured Osteosarcoma Cell Lines Using Chimeric Mouse/Human TP-1 IgG1 and IgG3 Antibodies," *Cancer Immunol. Immunother*. 48:411-418.
Schaefer, W. et al. (Jan. 2016). "Heavy and light Chain Pairing of Bivalent Quadroma and Knobs-Into-Holes Antibodies Analyzed by UHR-ESI-QTOF Mass Spectrometry," *mAbs* 8(1):49-55.
Schanzer, J.M. et al. (2016). "XGFR*, a Novel Affinity-Matured Bispecific Antibody Targeting IGF-1 R and EGFR With Combined

(56) References Cited

OTHER PUBLICATIONS

Signaling Inhibition and Enhanced Immune Activation for the Treatment of Pancreatic Cancer," *MABS* 8(4):811-827.

International Search Report dated Jan. 16, 2015, for PCT Application No. PCT/EP2014/071531, filed on Oct. 8, 2014, 6 pages.

Written Opinion dated Jan. 16, 2015, for PCT Application No. PCT/EP2014/071531, filed on Oct. 8, 2014, 5 pages.

International Preliminary Report on Patentability for PCT Application No. PCT/EP2014/079353, dated Jul. 12, 2016, filed Dec. 29, 2014, 9 pages.

International Search Report for PCT Application No. PCT/EP2014/079353, dated Apr. 4, 2015, filed Dec. 29, 2014, 6 pages.

Written Opinion International for PCT Application No. PCT/EP2014/079353, dated Jul. 12, 2016, filed Dec. 29, 2014, 9 pages.

International Search Report dated Aug. 5, 2014, for PCT Patent Application No. PCT/EP2013/063258, filed on Jun. 25, 2013, seven pages.

International Search Report dated Dec. 6, 2011, for PCT Patent Application No. PCT/EP2011/064476 filed on Aug. 23, 2011, seven pages.

\* cited by examiner

Antigen A

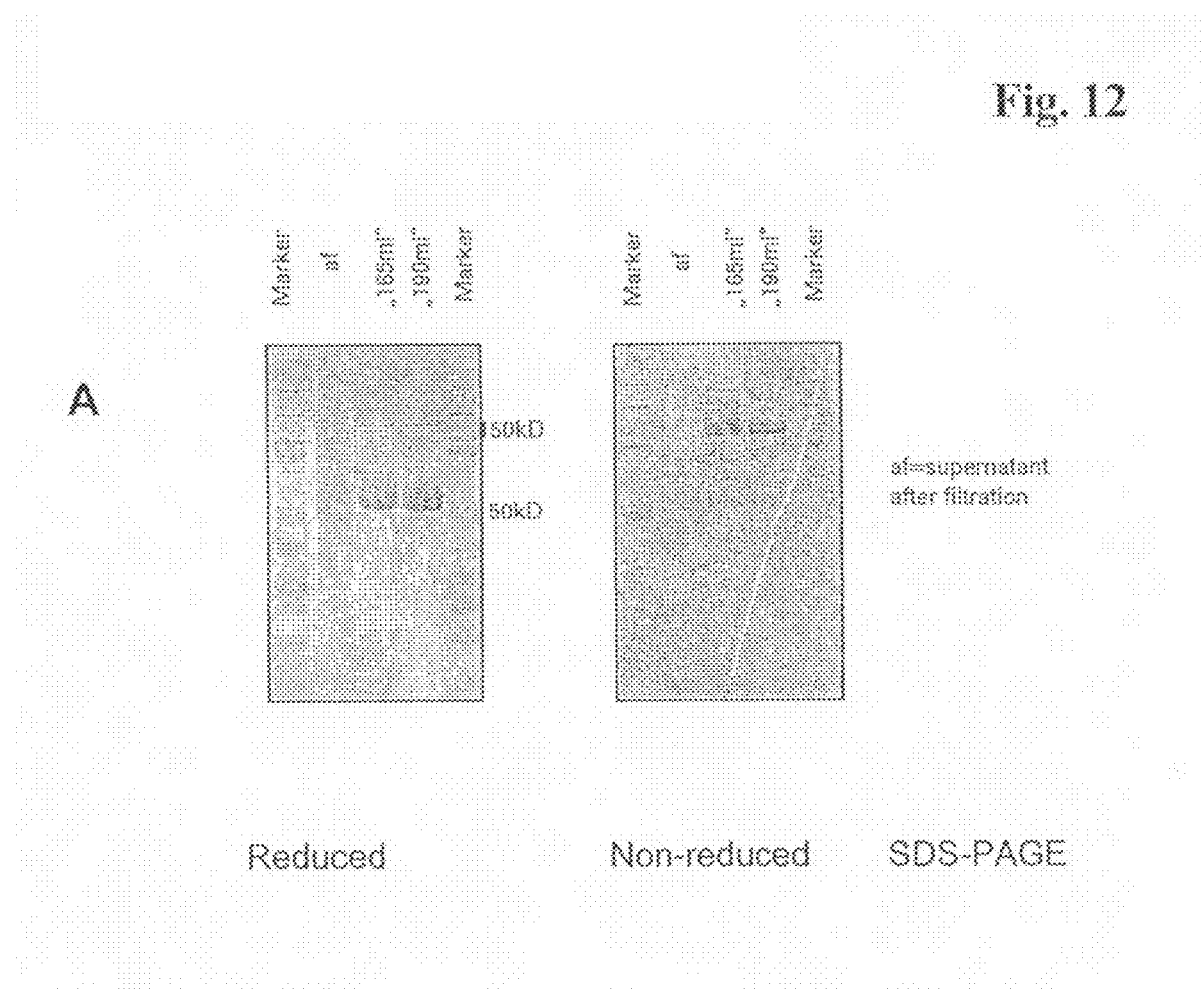

Binding of wildtype <IGF-1R> antibody to IGF-1R-ECD

Binding of <IGF-1R> VL-VH exchange antibody to IGF-1R-ECD

BIVALENT, BISPECIFIC ANTIBODIES

PRIORITY TO RELATED APPLICATION(S)

This application is a continuation of U.S. application Ser. No. 12/332,486, filed Dec. 11, 2008; which claims the benefit of European Patent Application No. 07024864.6, filed Dec. 21, 2007. The entire contents of the above-identified applications are hereby incorporated by reference.

BACKGROUND OF THE INVENTION

Engineered proteins, such as bi- or multispecific antibodies capable of binding two or more antigens are known in the art. Such multispecific binding proteins can be generated using cell fusion, chemical conjugation, or recombinant DNA techniques.

A wide variety of recombinant bispecific antibody formats have been developed in the recent past, e.g. tetravalent bispecific antibodies by fusion of, e.g. an IgG antibody format and single chain domains (see e.g. Morrison, S. L., et al, Nature Biotech 15 (1997) 159-163; WO2001077342; and Coloma, M. J., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger P, et al, Nature Biotech 23 (2005) 1126-1136 2005; Fischer N., Léger O., Pathobiology 74 (2007) 3-14; Shen J, et al, Journal of Immunological Methods 318 (2007) 65-74; Wu, C. et al Nature Biotech 25 (2007) 1290-1297)

All such formats use linkers either to fuse the antibody core (IgA, IgD, IgE, IgG or IgM) to a further binding protein (e.g. scFv) or to fuse e.g. two Fab fragments or scFv. (Fischer N., Léger O., Pathobiology 74 (2007) 3-14). While it is obvious that linkers have advantages for the engineering of bispecific antibodies, they may also cause problems in therapeutic settings. Indeed, these foreign peptides might elicit an immune response against the linker itself or the junction between the protein and the linker. Further more, the flexible nature of these peptides makes them more prone to proteolytic cleavage, potentially leading to poor antibody stability, aggregation and increased immunogenicity. In addition one may want to retain effector functions, such as e.g. complement-dependent cytotoxicity (CDC) or antibody dependent cellular cytotoxicity (ADCC), which are mediated through the Fcpart, by maintaining a high degree of similarity to naturally occurring antibodies.

Thus ideally, one should aim at developing bispecific antibodies that are very similar in general structure to naturally occurring antibodies (like IgA, IgD, IgE, IgG or IgM) with minimal deviation from human sequences.

In one approach bispecific antibodies that are very similar to natural antibodies have been produced using the quadroma technology (see Milstein, C. and A. C. Cuello, Nature, 305 (1983) 537-40) based on the somatic fusion of two different hybridoma cell lines expressing murine monoclonal antibodies with the desired specificities of the bispecific antibody. Because of the random pairing of two different antibody heavy and light chains within the resulting hybrid-hybridoma (or quadroma) cell line, up to ten different antibody species are generated of which only one is the desired, functional bispecific antibody. Due to the presence of mispaired byproducts, and significantly reduced production yields, means sophisticated purification procedures are required (see e.g. Morrison, S. L., Nature Biotech 25 (2007) 1233-1234). In general the same problem of mispaired byproducts remains if recombinant expression techniques are used.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway J B, Presta L G, Carter P; and WO1996027011). The percentage of heterodimer could be further increased by remodeling the interaction surfaces of the two CH3 domains using a phage display approach and the introduction of a disulfide bridge to stabilize the heterodimers (Merchant A. M, et al, Nature Biotech 16 (1998) 677-681; Atwell S, Ridgway J B, Wells J A, Carter P., J Mol Biol 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bivalent, bispecific antibodies against two antigens starting from two antibodies against the first and the second antigen, as either the heavy chains of these antibodies an/or the identical light chains have to be optimized.

Xie, Z., et al, J Immunol Methods 286 (2005) 95-101 refers to a new format of bispecific antibody using scFvs in combination with knobs-into-holes technology for the FC part.

SUMMARY OF THE INVENTION

The present invention relates to an isolated nucleic acid encoding the heavy chain of an antibody wherein the VH domain of said heavy chain is replaced by the VL domain of the corresponding light chain of said antibody.

The present invention also relates to an isolated nucleic acid encoding the light chain of an antibody wherein the VL domain of said light chain is replaced by the VH domain of the corresponding heavy chain of said antibody.

In addition, the present invention relates to an isolated nucleic acid encoding the heavy chain of an anti-angiopoietin-2 antibody wherein the constant heavy chain domain CH3 is altered or replaced by the CH1 domain of said heavy chain or the CL domain of the light chain for said antibody.

The present invention further relates to vectors comprising the aforementioned nucleic acids.

In addition, the present invention relates to a bivalent, bispecific antibody, comprising: (a) the light chain and heavy chain of an antibody specifically binding to a first antigen; and (b) the light chain and heavy chain of an antibody specifically binding to a second antigen, wherein the variable domains VL and VH from the antibody specifically binding to a second antigen are replaced by each other. The present invention also relates to a method for the preparation of such an antibody and a composition comprising such an antibody and at least one pharmaceutically acceptable excipient.

DETAILED DESCRIPTION OF THE INVENTION

The invention relates to a bivalent, bispecific antibody, comprising:
a) the light chain and heavy chain of an antibody specifically binding to a first antigen; and
b) the light chain and heavy chain of an antibody specifically binding to a second antigen, wherein the variable domains VL and VH from the antibody specifically binding to a second antigen are replaced by each other.

Therefore said bivalent, bispecific antibody, comprises:
a) a first light chain and a first heavy chain of an antibody specifically binding to a first antigen; and
b) a second light chain and a second heavy chain of an antibody specifically binding to a second antigen, wherein the variable domains VL and VH of the second light chain and the second heavy chain are replaced by each other.

Thus for said antibody specifically binding to a second antigen the following applies: within the light chain the variable light chain domain VL is replaced by the variable heavy chain domain VH of said antibody; and within the heavy chain the variable heavy chain domain VH is replaced by the variable light chain domain VL of said antibody.

The term "antibody" as used herein refers to whole, monoclonal antibodies. Such whole antibodies consist of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. In a whole antibody, each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The structure of one naturally occurring whole antibody, the IgG antibody, is shown e.g. in FIG. 1. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 ((Janeway C A, Jr et al (2001). Immunobiology., 5th ed., Garland Publishing; and Woof J, Burton D Nat Rev Immunol 4 (2004) 89-99). The two pairs of heavy chain and light chain (HC/LC) are capable of specifically binding to same antigen. Thus said whole antibody is a bivalent, monospecific antibody. Such "antibodies" include e.g. mouse antibodies, human antibodies, chimeric antibodies, humanized antibodies and genetically engineered antibodies (variant or mutant antibodies) as long as their characteristic properties are retained. Especially preferred are human or humanized antibodies, especially as recombinant human or humanized antibodies.

There are five types of mammalian antibody heavy chains denoted by the Greek letters: α, δ, ε, γ, and μ (Janeway C A, Jr et al (2001). Immunobiology., 5th ed., Garland Publishing). The type of heavy chain present defines the class of antibody; these chains are found in IgA, IgD, IgE, IgG, and IgM antibodies, respectively (Rhoades R A, Pflanzer R G (2002). Human Physiology, 4th ed., Thomson Learning). Distinct heavy chains differ in size and composition; α and γ contain approximately 450 amino acids, while μ and ε have approximately 550 amino acids.

Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof J, Burton D Nat Rev Immunol 4 (2004) 89-99); heavy chains μ and ε have a constant region composed of four constant domains CH1, CH2, CH3, and CH4 (Janeway C A, Jr et al (2001). Immunobiology., 5th ed., Garland Publishing). The variable region of the heavy chain differs in antibodies produced by different B cells, but is the same for all antibodies produced by a single B cell or B cell clone. The variable region of each heavy chain is approximately 110 amino acids long and is composed of a single antibody domain.

In mammals there are only two types of light chain, which are called lambda (λ) and kappa (κ). A light chain has two successive domains: one constant domain CL and one variable domain VL. The approximate length of a light chain is 211 to 217 amino acids. Preferably the light chain is a kappa (κ) light chain, and the constant domain CL is preferably derived from a kappa (κ) light chain (the constant domain Cκ)

The terms "monoclonal antibody" or "monoclonal antibody composition" as used herein refer to a preparation of antibody molecules of a single amino acid composition.

The "antibodies" according to the invention can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), whereby both antibodies, from which the bivalent bispecific antibody according to the invention is derived, have an Fc part of the same subclass (e.g. IgG1, IgG4 and the like, preferably IgG1), preferably of the same allotype (e.g. Caucasian)

A "Fc part of an antibody" is a term well known to the skilled artisan and defined on the basis of papain cleavage of antibodies. The antibodies according to the invention contain as Fc part, preferably a Fc part derived from human origin and preferably all other parts of the human constant regions. The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation, C1q binding and C3 activation, whereas IgG4 do not activate the complement system, do not bind C1q and do not activate C3. Preferably the Fc part is a human Fc part.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

The "constant domains" of the heavy chain and of the light chain are not involved directly in binding of an antibody to an antigen, but exhibit various effector functions. Depending on the amino acid sequence of the constant region of their heavy chains, antibodies or immunoglobulins are divided into the classes:

The term "bivalent, bispecific antibody" as used herein refers to an antibody as described above in which each of the two pairs of heavy chain and light chain (HC/LC) is specifically binding to a different antigen, i.e. the first heavy and the first light chain (originating from an antibody against a first antigen) are specifically binding together to a first antigen, and, the second heavy and the second light chain (originating from an antibody against a second antigen) are specifically binding together to a second antigen (as depicted in FIG. 2); such bivalent, bispecific antibodies are capable of specifically binding to two different antigens at the same time, and not to more than two antigens, in contrary to, on the one hand a monospecific antibody capable of binding only to one antigen, and on the other hand e.g. a tetravalent, tetraspecific antibody which can bind to four antigen molecules at the same time.

According to the invention, the ratio of a desired bivalent, bispecific antibody compared to undesired side products can be improved by the replacement of certain domains in only one pair of heavy chain and light chain (HC/LC). While the first of the two HC/LC pairs originates from an antibody specifically binding to a first antigen and is left essentially unchanged, the second of the two HC/LC pairs originates from an antibody specifically binding to a second antigen, and is altered by the following replacement:

light chain: replacement of the variable light chain domain VL by the variable heavy chain domain VH of said antibody specifically binding to a second antigen, and heavy chain: replacement of the variable heavy chain domain VH by the variable light chain domain VL of said antibody specifically binding to a second antigen.

Thus the resulting bivalent, bispecific antibodies are artificial antibodies which comprise
a) the light chain and heavy chain of an antibody specifically binding to a first antigen; and
b) the light chain and heavy chain of an antibody specifically binding to a second antigen, wherein said light chain (of an antibody specifically binding to a second antigen) contains a variable domain VH instead of VL, and
wherein said heavy chain (of an antibody specifically binding to a second antigen) contains a variable domain VL instead of VH.

In an additional aspect of the invention such improved ratio of a desired bivalent, bispecific antibody compared to undesired side products can be further improved by one of the following two alternatives:
A) First Alternative (see FIG. 3):

The CH3 domains of said bivalent, bispecific antibody according to the invention can be altered by the "knob-into-holes" technology which described with in detail with several examples in e.g. WO96/027011, Ridgway J B, et al, Protein Eng 9 (1996) 617-621; and Merchant A. M., et al, Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant A. M, et al, Nature Biotech 16 (1998) 677-681; Atwell S, Ridgway J B, Wells J A, Carter P., J Mol Biol 270 (1997) 26-35) and increases the yield.

Therefore in preferred embodiment the CH3 domains of a bivalent, bispecific antibody wherein the first CH3 domain and second CH3 domain each meet at an interface which comprises an original interface between the antibody CH3 domains are altered by the "knob-into-holes" technology including further stabilization by introduction of a disulfide bridge in the CH3 domains (described in WO96/027011, Ridgway J B, et al, Protein Eng 9 (1996) 617-621; Merchant A. M, et al, Nature Biotech 16 (1998) 677-681; and Atwell S, Ridgway J B, Wells J A, Carter P., J Mol Biol 270 (1997) 26-35) to promote the formation of the bivalent, bispecific antibody.

Thus in one aspect of the invention said bivalent, bispecific antibody is characterized in that
the CH3 domain of one heavy chain and the CH3 domain of the other heavy chain each meet at an interface which comprises an original interface between the antibody CH3 domains; wherein said interface is altered to promote the formation of the bivalent, bispecific antibody, wherein the alteration is characterized in that:
a) the CH3 domain of one heavy chain is altered,
so that within the original interface the CH3 domain of one heavy chain that meets the original interface of the CH3 domain of the other heavy chain within the bivalent, bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
b) the CH3 domain of the other heavy chain is altered,
so that within the original interface of the second CH3 domain that meets the original interface of the first CH3 domain within the bivalent, bispecific antibody
an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered the introduction of cysteine (C) as amino acid in the corresponding positions of each CH3 domain such that a disulfide bridge between both CH3 domains can be formed.

In another preferred embodiment of the invention both CH3 domains are altered by the use of residues R409D; K370E (K409D) for knobs residues and D399K; E357K for hole residues described eg. in EP 1870459A1;
or
B) Second Alternative (see FIG. 4):

by the replacement of one constant heavy chain domain CH3 by a constant heavy chain domain CH1; and the other constant heavy chain domain CH3 is replaced by a constant light chain domain CL.

The constant heavy chain domain CH1 by which the heavy chain domain CH3 is replaced can be of any Ig class (e.g. IgA, IgD, IgE, IgG, and IgM), or subclass (e.g., IgG1, IgG2, IgG3, IgG4, IgA1 and IgA2).

The constant light chain domain CL by which the heavy chain domain CH3 is replaced can be of the lambda (λ) or kappa (κ) type, preferably the kappa (κ) type.

Thus one preferred embodiment of the invention is a bivalent, bispecific antibody, comprising:
a) the light chain and heavy chain of an antibody specifically binding to a first antigen; and
b) the light chain and heavy chain of an antibody specifically binding to a second antigen, wherein the variable domains VL and VH are replaced by each other, and wherein optionally c) the CH3 domain of one heavy chain and the CH3 domain of the other heavy chain each meet at an interface which comprises an original interface between the antibody CH3 domains; wherein said interface is altered to promote the formation of the bivalent, bispecific antibody-,
wherein the alteration is characterized in that:
ca) the CH3 domain of one heavy chain is altered,
so that within the original interface the CH3 domain of one heavy chain that meets the original interface of the CH3 domain of the other heavy chain within the bivalent, bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
cb) the CH3 domain of the other heavy chain is altered,
so that within the original interface of the second CH3 domain that meets the original interface of the first CH3 domain within the bivalent, bispecific antibody
an amino acid residue is replaced with an amino acid residue having a smaller side chain volume, thereby generating a cavity within the interface of the second CH3 domain within which a protuberance within the interface of the first CH3 domain is positionable;
or
d) one constant heavy chain domain CH3 is replaced by a constant heavy chain domain CH1; and the other constant heavy chain domain CH3 is replaced by a constant light chain domain CL.

The terms "antigen" or "antigen molecule" as used herein are used interchangeable and refer to all molecules that can be specifically bound by an antibody. The bivalent, bispecific antibody is specifically binding to a first antigen and a second distinct antigen. The term "antigens" as used herein include e.g. proteins, different epitopes on proteins (as different antigens within the meaning of the invention), and polysaccharides. This mainly includes parts (coats, capsules, cell walls, flagella, fimbrae, and toxins) of bacteria, viruses, and other microorganisms. Lipids and nucleic acids are antigenic only when combined with proteins and polysaccharides. Non-microbial exogenous (non-self) antigens can include pollen, egg white, and proteins from transplanted tissues and organs or on the surface of transfused blood cells. Preferably the antigen is selected from the group consisting of cytokines, cell surface proteins, enzymes and receptors cytokines, cell surface proteins, enzymes and receptors.

Tumor antigens are those antigens that are presented by MHC I or MHC II molecules on the surface of tumor cells. These antigens can sometimes be presented by tumor cells and never by the normal ones. In this case, they are called tumor-specific antigens (TSAs) and typically result from a tumor specific mutation. More common are antigens that are presented by tumor cells and normal cells, and they are called tumor-associated antigens (TAAs). Cytotoxic T lymphocytes that recognized these antigens may be able to destroy the tumor cells before they proliferate or metastasize. Tumor antigens can also be on the surface of the tumor in the form of, for example, a mutated receptor, in which case they will be recognized by B cells.

In one preferred embodiment at least one of the two different antigens (first and second antigen), to which the bivalent, bispecific antibody specifically binds to, is a tumor antigen.

In another preferred embodiment both of the two different antigens (first and second antigen), to which the bivalent, bispecific antibody specifically binds to, are tumor antigens; in this case the first and second antigen can also be two different epitopes at the same tumor specific protein.

In another preferred embodiment one of the two different antigens (first and second antigen), to which the bivalent, bispecific antibody specifically binds to, is a tumor antigen and the other is an effector cell antigen, as e.g. an T-Cell receptor, CD3, CD16 and the like.

In another preferred embodiment one of the two different antigens (first and second antigen), to which the bivalent, bispecific antibody specifically binds to, is a tumor antigen and the other is an anti-cancer substance such as a toxin or a kinase inhibitor.

As used herein, "specifically binding" or "binds specifically to" refers to an antibody specifically binding an antigen. Preferably the binding affinity of the antibody specifically binding this antigen is of KD-value of $10^{-9}$ mol/l or lower (e.g. $10^{-10}$ mol/l), preferably with a KD-value of $10^{-10}$ mol/l or lower (e.g. $10^{-12}$ mol/l). The binding affinity is determined with a standard binding assay, such as surface plasmon resonance technique (Biacore®).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

An further embodiment of the invention is a method for the preparation of a bivalent, bispecific antibody according to the invention comprising
a) transforming a host cell with
vectors comprising nucleic acid molecules encoding the light chain and heavy chain of an antibody specifically binding to a first antigen
vectors comprising nucleic acid molecules encoding the light chain and heavy chain of an antibody specifically binding to a second antigen, wherein the variable domains VL and VH are replaced by each other;
b) culturing the host cell under conditions that allow synthesis of said antibody molecule; and
c) recovering said antibody molecule from said culture.

In general there are two vectors encoding the light chain and heavy chain of said antibody specifically binding to a first antigen, and further two vectors encoding the light chain and heavy chain of said antibody specifically binding to a second antigen. One of the two vectors is encoding the respective light chain and the other of the two vectors is encoding the respective heavy chain. However in an alternative method for the preparation of a bivalent, bispecific antibody according to the invention, only one first vector encoding the light chain and heavy chain of the antibody specifically binding to a first antigen and only one second vector encoding the light chain and heavy chain of the antibody specifically binding to a second antigen can be used for transforming the host cell.

The invention encompasses a method for the preparation of the antibodies comprising culturing the corresponding host cells under conditions that allow synthesis of said antibody molecules and recovering said antibodies from said culture, e.g. by expressing a first nucleic acid sequence encoding the light chain of an antibody specifically binding to a first antigen, a second nucleic acid sequence encoding the heavy chain of said antibody specifically binding to a first antigen, a third nucleic acid sequence encoding the light chain of an antibody specifically binding to a second antigen, wherein the variable light chain domain VL is replaced by the variable heavy chain domain VH, and a fourth nucleic acid sequence encoding the heavy chain of said antibody specifically binding to a second antigen, wherein variable heavy chain domain VH by the variable light chain domain VL.

A further embodiment of the invention is a host cell comprising vectors comprising nucleic acid molecules encoding the light chain and heavy chain of an antibody specifically binding to a first antigen vectors comprising nucleic acid molecules encoding the light chain and heavy chain of an antibody specifically binding to a second antigen, wherein the variable domains VL and VH are replaced by each other.

A further embodiment of the invention is a host cell comprising a) a vector comprising a nucleic acid molecule encoding the light chain and a vector comprising a nucleic acid molecule encoding the heavy chain, of an antibody specifically binding to a first antigen b) a vector comprising a nucleic acid molecule encoding the light chain and a vector comprising a nucleic acid molecule encoding the heavy chain, of an antibody specifically binding to a second antigen, wherein the variable domains VL and VH are replaced by each other.

A further embodiment of the invention is a composition, preferably a pharmaceutical or a diagnostic composition of the bivalent, bispecific antibody according to the invention.

A further embodiment of the invention is a pharmaceutical composition comprising a bivalent, bispecific antibody according to the invention and at least one pharmaceutically acceptable excipient.

A further embodiment of the invention is a method for the treatment of a patient in need of therapy, characterized by administering to the patient a therapeutically effective amount of a bivalent, bispecific antibody according to the invention.

The term "nucleic acid or nucleic acid molecule", as used herein, is intended to include DNA molecules and RNA molecules. A nucleic acid molecule may be single-stranded or double-stranded, but preferably is double-stranded DNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, F. N, et al, PNAS. 69 (1972) 7110ff.

Recombinant production of antibodies using transformation is well-known in the state of the art and described, for example, in the review articles of Makrides, S. C., Protein Expr. Purif 17 (1999) 183-202; Geisse, S., et al., Protein Expr. Purif. 8 (1996) 271-282; Kaufman, R. J., Mol. Biotechnol. 16 (2000) 151-161; Werner, R. G., et al., Arzneimittelforschung 48 (1998) 870-880 as well as in U.S. Pat. No. 6,331,415 and U.S. Pat. No. 4,816,567.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The bivalent, bispecific antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis). The bivalent, bispecific antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The bivalent, bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA or RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bivalent, bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The following examples, sequence listing and figures are provided to aid the understanding of the present invention, the true scope of which is set forth in the appended claims. It is understood that modifications can be made in the procedures set forth without departing from the spirit of the invention.

SEQUENCE LISTING

SEQ ID NO: 1 amino acid sequence of wild type <IGF-1R> antibody heavy chain
SEQ ID NO: 2 amino acid sequence of wild type <IGF-1R> antibody light chain
SEQ ID NO: 3 amino acid sequence of the heavy chain* (HC*) of <IGF-1R> VL-VH exchange antibody, wherein the heavy chain domain VH is replaced by the light chain domain VL-variant A.
SEQ ID NO: 4 amino acid sequence of the light chain* (LC*) of <IGF-1R> VL-VH exchange antibody, wherein the light chain domain VL is replaced by the heavy chain domain VH-variant A.
SEQ ID NO: 5 amino acid sequence of IGF-1R ectodomain His-Streptavidin binding peptide-tag (IGF-1R-His-SBP ECD)
SEQ ID NO: 6 amino acid sequence of wild type Angiopoietin-2 <ANGPT2> antibody heavy chain
SEQ ID NO: 7 amino acid sequence of wild type Angiopoietin-2 <ANGPT2> antibody light chain
SEQ ID NO: 8 amino acid sequence of CH3 domain (Knobs) with a T366W exchange for use in the knobs-into-holes technology
SEQ ID NO: 9 amino acid sequence CH3 domain (Hole) with a T366S, L368A, Y407V exchange for use in the knobs-into-holes technology
SEQ ID NO: 10 amino acid sequence of the heavy chain* (HC*) of <IGF-1R> VL-VH exchange antibody, wherein the heavy chain domain VH is replaced by the light chain domain VL-variant B.
SEQ ID NO: 11 amino acid sequence of the light chain* (LC*) of <IGF-1R> VL-VH exchange antibody, wherein the light chain domain VL is replaced by the heavy chain domain VH-variant B.
SEQ ID NO: 12 amino acid sequence of IGF-1R ectodomain His-Streptavidin binding peptide-tag (IGF-1R-His-SBP ECD)

Figure 1:
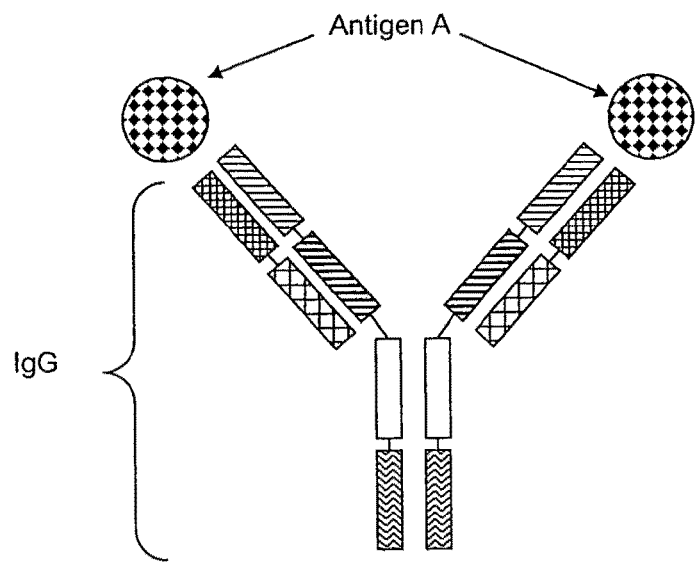
FIG. 1 Schematic figure of IgG, a naturally occurring whole antibody specific for one antigen with two pairs of heavy and light chain which comprise variable and constant domains in a typical order.
Figure 1:
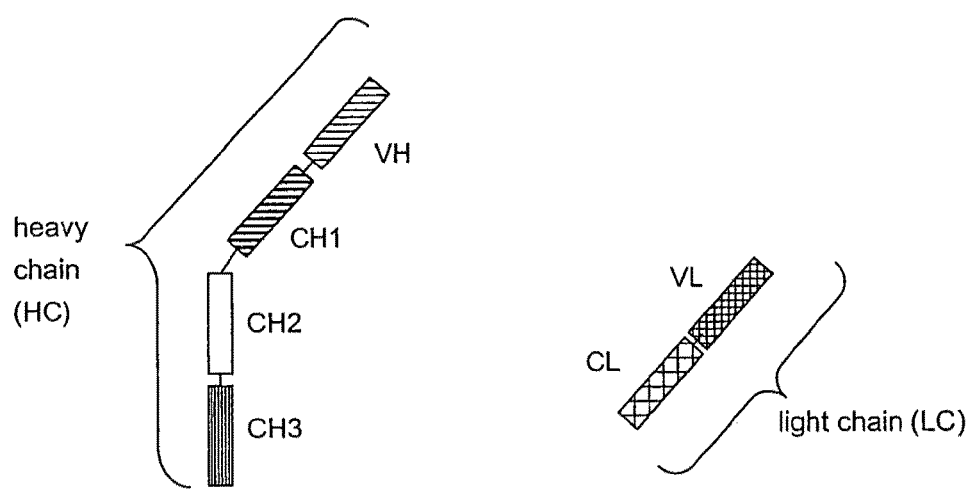
Figure 1:
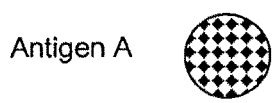
Figure 2:
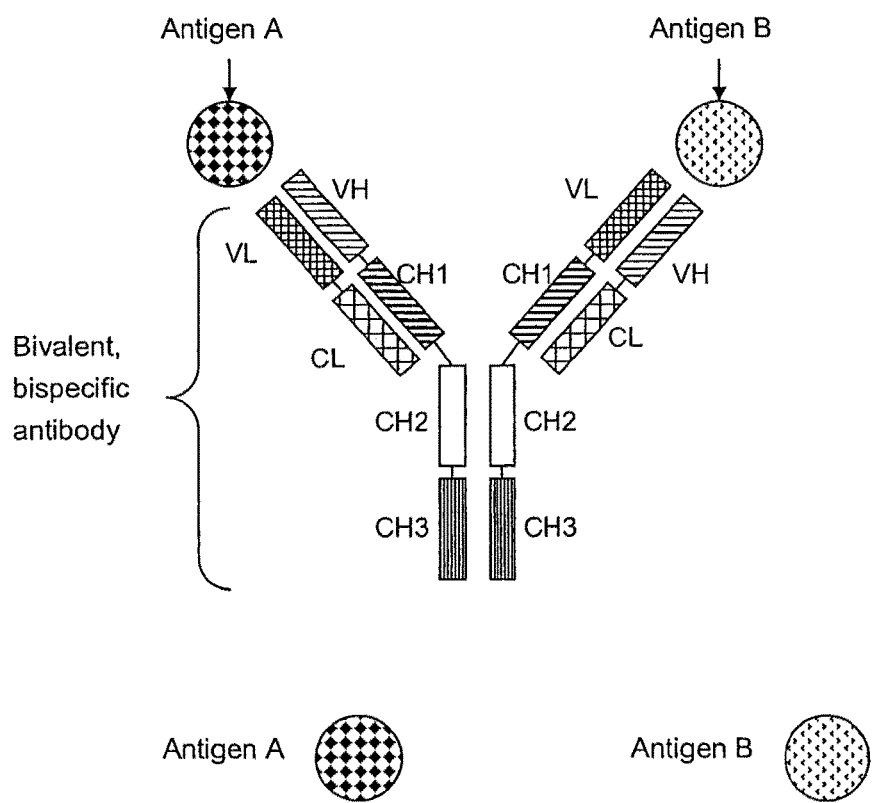
FIG. 2 Schematic figure of a bivalent, bispecific antibody, comprising: a) the light chain and heavy chain of an antibody specifically binding to a first antigen; and b) the light chain and heavy chain of an antibody specifically binding to a second antigen, wherein the variable domains VL and VH are replaced by each other.
Figure 3:
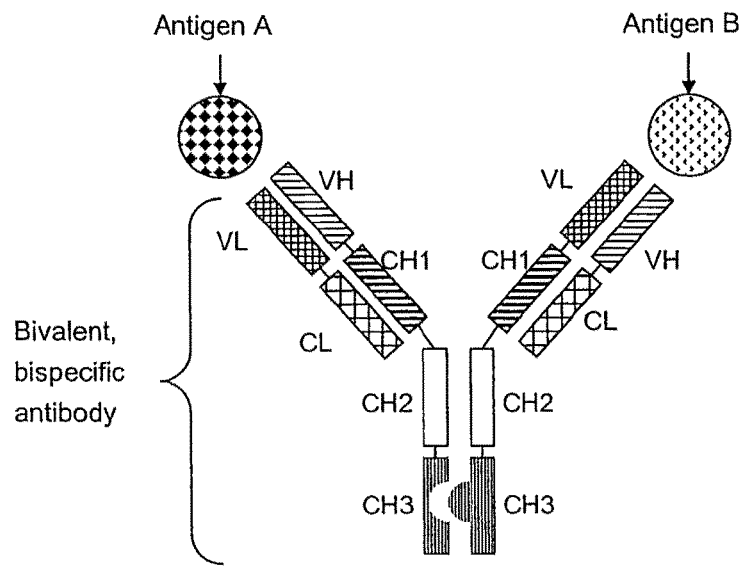
FIG. 3 Schematic figures of bivalent, bispecific antibodies, comprising: the light chain and heavy chain of an antibody specifically binding to a first antigen; and the light chain and heavy chain of an antibody specifically binding to a second antigen, wherein the variable domains VL and VH are replaced by each other, and wherein the CH3 domains of both heavy chains are altered by the knobs-into-holes technology. In the antibody of the top schematic, the CH3 domain of the heavy chain on the right has the "knob" and the CH3 domain of the heavy chain on the left has the "hole". In the antibody of the bottom schematic, the CH3 domain of the heavy chain on the left has the "knob" and the CH3 domain of the heavy chain on the right has the "hole".
Figure 3:
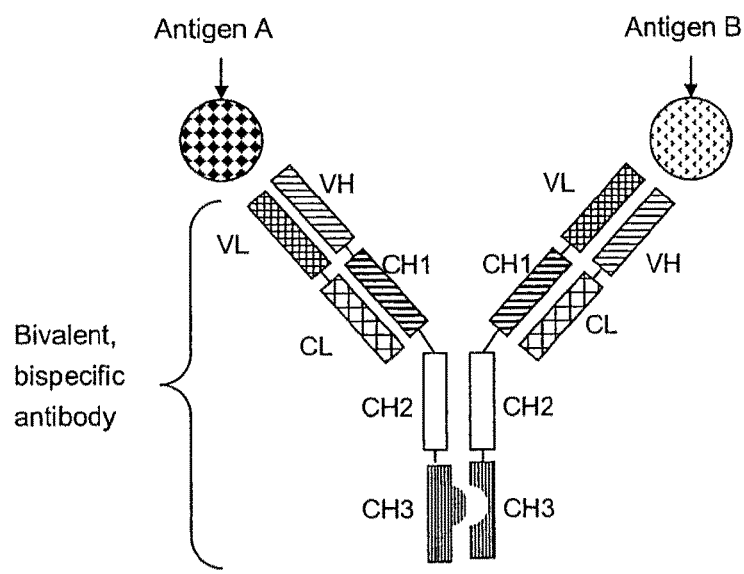
Figure 3:
Figure 4:
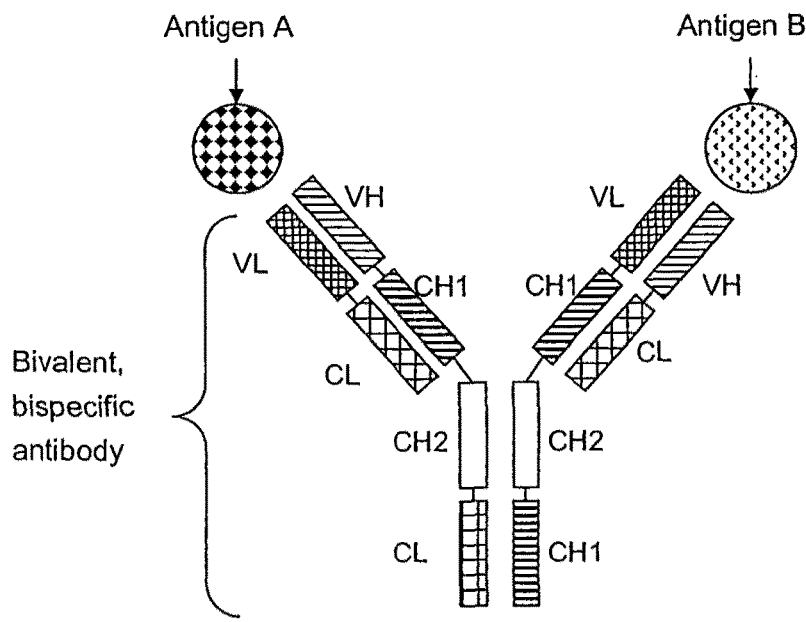
FIG. 4 Schematic figures of bivalent, bispecific antibodies, comprising: the light chain and heavy chain of an antibody specifically binding to a first antigen; and the light chain and heavy chain of an antibody specifically binding to a second antigen, wherein the variable domains VL and VU are replaced by each other, and where n one of the constant heavy chain domains CH3 of both heavy chains is replaced by a constant heavy chain domain CH1; and the other constant heavy chain domain CH3 is replaced by a constant light chain domain CL. In the antibody of the top schematic, the CH3 domain of the heavy chain on the right has been replaced by a CH1 domain and the CH3 domain of the heavy chain on the left has been replaced by a CL domain the antibody of the bottom schematic, the CH3 domain of the heavy chain on the left has been replaced by a CH1 domain and the CH3 domain of the heavy chain on the right has been replaced by a CL domain.
Figure 4:
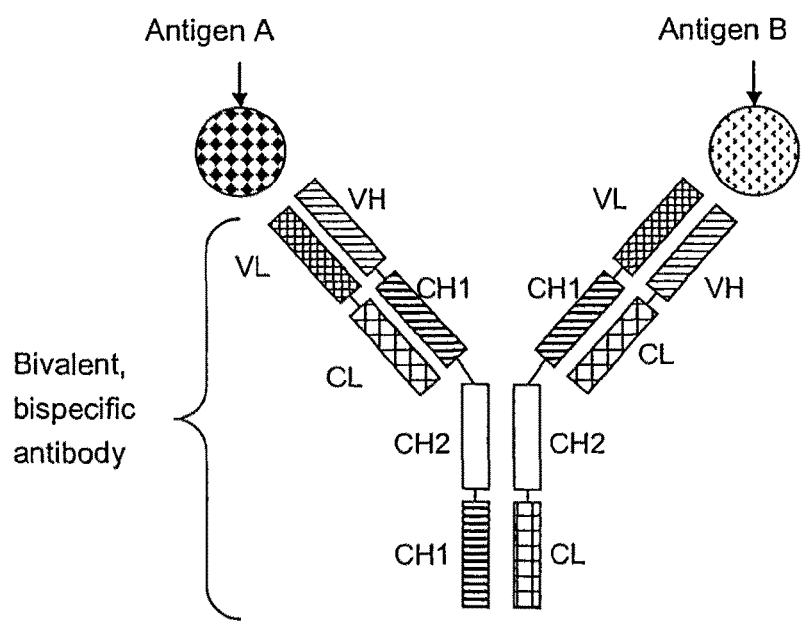

A=I24 untreated
B=I24+2 µg/mL hANGPT2 hIgG isotype
D=I24+2 µg/mL hANGPT2+Mix from co-expression of <IGF-1R> VL-VH exchange antibody and <ANGPT2> wildtype antibody comprising bispecific <ANGPT2-IGF-1R> VL-VH exchange antibody
E=I24+2 µg/mL hANGPT2<ANGPT2> wildtype antibody
F=I24+2 µg/mL hANGPT2<IGF-1R> wildtype antibody.

EXAMPLES

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 600-1800 bp long gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies variants of expression plasmids for transient expression (e.g. in HEK293 EBNA or HEK293-F) cells based either on a cDNA organization with a CMV-Intron A promoter or on a genomic organization with a CMV promoter were applied.

Beside the antibody expression cassette the vectors contained:
an origin of replication which allows replication of this plasmid in E. coli, and
a β-lactamase gene which confers ampicillin resistance in E. coli.

The transcription unit of the antibody gene is composed of the following elements:
unique restriction site(s) at the 5' end
the immediate early enhancer and promoter from the human cytomegalovirus,
followed by the Intron A sequence in the case of the cDNA organization,
a 5'-untranslated region of a human antibody gene,
a immunoglobulin heavy chain signal sequence,
the human antibody chain (wildtype or with domain exchange) either as cDNA or as genomic organization with an the immunoglobulin exon-intron organization
a 3' untranslated region with a polyadenylation signal sequence, and
unique restriction site(s) at the 3' end.

The fusion genes comprising the described antibody chains as described below were generated by PCR and/or gene synthesis and assembled with known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed E. coli cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Bispecific antibodies were expressed by transient co-transfection of the respective expression plasmids in adherently growing HEK293-EBNA or in HEK29-F cells growing in suspension as described below.

Transient Transfections in HEK293-EBNA System

Bispecific antibodies were expressed by transient co-transfection of the respective expression plasmids (e.g. encoding the heavy and modified heavy chain, as well as the corresponding light and modified light chain) in adherently growing HEK293-EBNA cells (human embryonic kidney cell line 293 expressing Epstein-Barr-Virus nuclear antigen; American type culture collection deposit number ATCC #CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 µg/ml Geneticin (Gibco). For transfection FuGENE™ 6 Transfection Reagent (Roche Molecular Biochemicals) was used in a ratio of FuGENE™ reagent (µl) to DNA (µg) of 4:1 (ranging from 3:1 to 6:1). Proteins were expressed from the respective plasmids using a molar ratio of (modified and wildtype) light chain and heavy chain encoding plasmids of 1:1 (equimolar) ranging from 1:2 to 2:1, respectively. Cells were fed at day 3 with L-Glutamine ad 4 mM, Glucose [Sigma] and NAA [Gibco]. Bispecific antibody containing cell culture supernatants were harvested from day 5 to 11 after transfection by centrifugation and stored at −20° C. General information regarding the recombinant expression of human immunoglobulins in e.g. HEK293 cells is given in: Meissner, P. et al., Biotechnol. Bioeng. 75 (2001) 197-203.

Transient Transfections in HEK293-F System

Bispecific antibodies were generated by transient transfection of the respective plasmids (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serumfree FreeStyle 293 expression medium (Invitrogen) were transfected with a mix of the four expression plasmids and 293fectin or fectin (Invitrogen). For 2 L shake flask (Corning) HEK293-F cells were seeded at a density of 1.0E*6 cells/mL in 600 mL and incubated at 120 rpm, 8% CO2. The day after the cells were transfected at a cell density of ca. 1.5E*6 cells/mL with ca. 42 mL mix of A) 20 mL Opti-MEM (Invitrogen) with 600 µg total plasmid DNA (1 µg/mL) encoding the heavy or modified heavy chain, respectively and the corresponding light chain in an equimolar ratio and B) 20 ml Opti-MEM+1.2 mL 293 fectin or fectin (2 µl/mL). According to the glucose consumption glucose solution was added during the course of the fermentation. The supernatant containing the secreted antibody was harvested after 5-10 days and antibodies were either directly purified from the supernatant or the supernatant was frozen and stored.

Protein Determination

The protein concentration of purified antibodies and derivatives was determined by determining the optical density (OD) at 280 nm, using the molar extinction coefficient calculated on the basis of the amino acid sequence according to Pace et al., Protein Science, 1995, 4, 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads are washed three times in TBS-NP40 (50 mM Tris, pH 7.5, 150 mM NaCl, 1% Nonidet-P40). Subsequently, 1-15 mL cell culture supernatant were applied to the Protein A Agarose beads pre-equilibrated in TBS-NP40. After incubation for at 1 h at room temperature the beads were washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5.0. Bound antibody was eluted by addition of 35 µl A NuPAGE® LDS Sample Buffer (Invitrogen). Half of the sample was combined with NuPAGE® Sample Reducing Agent or left unreduced, respectively, and heated for 10 min at 70° C. Consequently, 5-30 µl were applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was quantitatively measured by affinity HPLC chromatography. Briefly, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an Agilent HPLC 1100 system. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 µL/well biotinylated anti-human IgG capture molecule F(ab')2<h-Fcγ> BI (Dianova) at 0.1 µg/mL for 1 h at room temperature or alternatively over night at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 h on a microtiterplate shaker at room temperature. The wells were washed three times with 200 µL/well PBST and bound antibody was detected with 100 µl F(ab')2<hFcγ>POD (Dianova) at 0.1 µg/mL as detection antibody for 1-2 h on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated if required using e.g. a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

The total deglycosylated mass of crossover antibodies was determined and confirmed via electrospray ionization mass spectrometry (ESI-MS). Briefly, 100 µg purified antibodies were deglycosylated with 50 mU N-Glycosidase F (PNGaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 µg antibody in 115 µl were incubated with 60 µl 1M TCEP and 50 µl 8 M Guanidine-hydrochloride subsequently desalted. The total mass and the mass of the reduced heavy and light chains was determined via ESI-MS on a Q-Star Elite MS system equipped with a NanoMate source.

IGF-1R ECD Binding ELISA

The binding properties of the generated antibodies were evaluated in an ELISA assay with the IGF-1R extracellular domain (ECD). For this sake the extracellular domain of IGF-1R (residues 1-462) comprising the natural leader sequence and the LI-cysteine rich-12 domains of the human IGF-IR ectodomain of the alpha chain (according to the McKern et al., 1997; Ward et al., 2001) fused to an N-terminal His-Streptavidin binding peptide-tag (His-SBP) was cloned into a pcDNA3 vector derivative and transiently expressed in HEK293F cells. The protein sequence of the IGF-1R-His-SBP ECD is given in SEQ ID NO: 12. StreptaWell High Bind Strepatavidin A-96 well microtiter plates (Roche) were coated with 100 µL/well cell culture supernatant containing soluble IGF-1R-ECD-SBP fusion protein over night at 4° C. and washed three times with 200 µL/well PBS, 0.05% Tween (PBST, Sigma). Subsequently, 100 µL/well of a dilution series of the respective antibody and as a reference wildtype <IGF-1R> antibody in PBS (Sigma) including 1% BSA (fraction V, Roche) was added to the wells and incubated for 1-2 h on a microtiterplate shaker at room temperature. For the dilution series the same amount of purified antibody were applied to the wells. The wells were washed three times with 200 µL/well PBST and bound antibody was detected with 100 µL/well F(ab')2<hFcγ>POD (Dianova) at 0.1 µg/mL (1:8000) as detection antibody for 1-2 h on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

IGF-1R ECD Biacore

Figure 11:
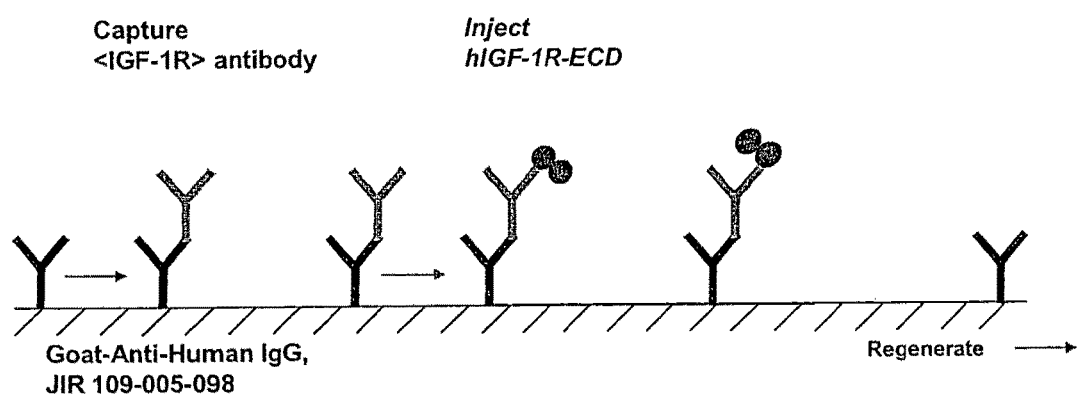

Binding of the generated antibodies to human IGF-1R ECD was also investigated by surface plasmon resonance using a BIACORE T100 instrument (GE Healthcare Biosciences AB, Uppsala, Sweden). Briefly, for affinity measurements Goat-Anti-Human IgG, JIR 109-005-098 antibodies were immobilized on a CM5 chip via amine coupling for presentation of the antibodies against human IGF-1R ECD-Fc tagged. Binding was measured in HBS buffer (HBS-P (10 mM HEPES, 150 mM NaCl, 0.005% Tween 20, ph 7.4), 25° C. IGF-1R ECD (R&D Systems or in house purified) was added in various concentrations in solution. Association was measured by an IGF-1R ECD injection of 80 seconds to 3 minutes; dissociation was measured by washing the chip surface with HBS buffer for 3-10 minutes and a KD value was estimated using a 1:1 Langmuir binding model. Due to low loading density and capturing level of <IGF-1R> antibodies monovalent IGF-1R ECD binding was obtained. Negative control data (e.g. buffer curves) were subtracted from sample curves for correction of system intrinsic baseline drift and for noise signal reduction. Biacore T100 Evaluation Software version 1.1.1 was used for analysis of sensorgrams and for calculation of affinity data. FIG. 11 shows a scheme of the Biacore assay.

Examples 1

Production, Expression, Purification and Characterization of Monospecific, Bivalent <IGF-1R> Antibody, Wherein the Variable Domains VL and VH are Replaced by Each Other (Abbreviated Herein as <IGF-1R> VL-VH Exchange Antibody)

Example 1A

Making of the Expression Plasmids for the Monospecific, Bivalent <IGF-1R> VL-VH Exchange Antibody The sequences for the heavy and light chain variable domains of the monospecific, bivalent <IGF-1R> VL-VH exchange antibody including the respective leader sequences described in this example are derived from a human <IGF-1R> antibody heavy chain (SEQ ID NO: 1, plasmid 4843-pUC-HC-IGF-1R) and a light chain (SEQ ID NO: 2, plasmid 4842-pUC-LC-IGF-1R) described in WO 2005/005635, and the heavy and light chain constant domains are derived from a human antibody (C-kappa and IgG1).

The gene segments encoding the <IGF-1R> antibody leader sequence, light chain variable domain (VL) and the human heavy chain constant domain 1 (CH1) were joined and fused to the 5'-end of the Fc domains of the human γ1-heavy chain constant domains (Hinge-CH2-CH3). The DNA coding for the respective fusion protein resulting from the exchange of the VH domain by the VL domain (VH-VL exchange) was generated by gene synthesis and is denoted <IGF-1R> HC* (SEQ ID NO: 10) in the following. Initially, the VL-CH1 domains were fused with a slightly different sequence (SEQ ID NO: 3); due to the reduced expression yields of this connection, SEQ10 that shows expression yields comparable to wildtype antibodies, was chosen. The gene segments for the <IGF-1R> antibody leader sequence, heavy chain variable domain (VH) and the human light chain constant domain (CL) were joined as independent chain. The DNA coding for the respective fusion protein resulting from the exchange of the VL domain by the VH domain (VL-VH exchange) was generated by gene synthesis and is denoted <IGF-1R> LC* (Heavy Chain***) (SEQ ID NO: 11) in the following. Initially, the VH-CL domains were fused with a slightly different sequence (SEQ ID NO: 4); due to the reduced expression yields of this connection, SEQ ID NO: 11 that shows expression yields comparable to wildtype antibodies was chosen.

Figure 5:
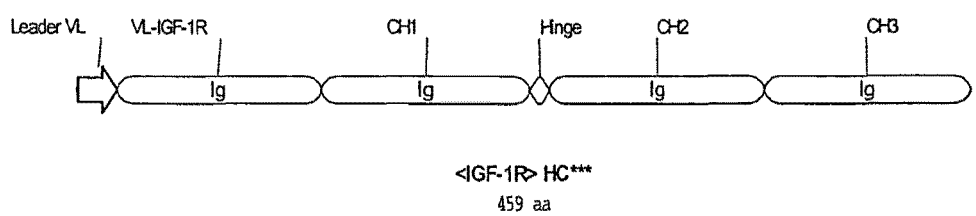
FIG. 5 Protein sequence scheme of the heavy chain*<IGF-1R> HC* of the <IGF-1R> VL-VH exchange antibody FIG. 6 Protein sequence scheme of the light chain*<IGF-1R> LC* of the <IGF-1R> VL-VH exchange antibody (with a kappa constant light chain domain CL)
Figure 6:
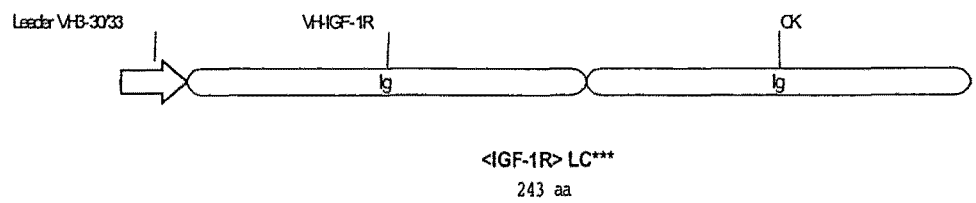

FIG. 5 and FIG. 6 show a schematic view of the protein sequence of the modified <IGF-1R> HC* heavy chain and the modified <IGF-1R> LC* light chain.

In the following the respective expression vectors are briefly described:

Vector pUC-HC***-IGF-1R

Vector pUC-HC*-IGF-1R is an expression plasmid e.g. for transient expression of a VL-VH exchange <IGF-1R> heavy chain HC* (cDNA organized expression cassette; with CMV-Intron A) in HEK293 (EBNA) cells or for stable expression in CHO cells.

Beside the <IGF-1R> HC*** expression cassette this vector contains:

an origin of replication from the vector pUC18 which allows replication of this plasmid in *E. coli*, and a β-lactamase gene which confers ampicillin resistance in *E. coli*.

The transcription unit of the <IGF-1R> HC*** gene is composed of the following elements:

the AscI restriction site at the 5'-end the immediate early enhancer and promoter from the human cytomegalovirus, followed by the Intron A sequence, a 5'-untranslated region of a human antibody gene, a immunoglobulin light chain signal sequence, the human <IGF-1R> mature HC*** chain encoding a fusion of the human heavy chain variable domain (VH) and the human kappa-light chain constant domain (CL) fused to the 5'-end of the Fc domains of the human γ1-heavy chain constant domains (Hinge-CH2-CH3).

a 3' untranslated region with a polyadenylation signal sequence, and the restriction site SgrAI at the 3'-end.

Figure 7:
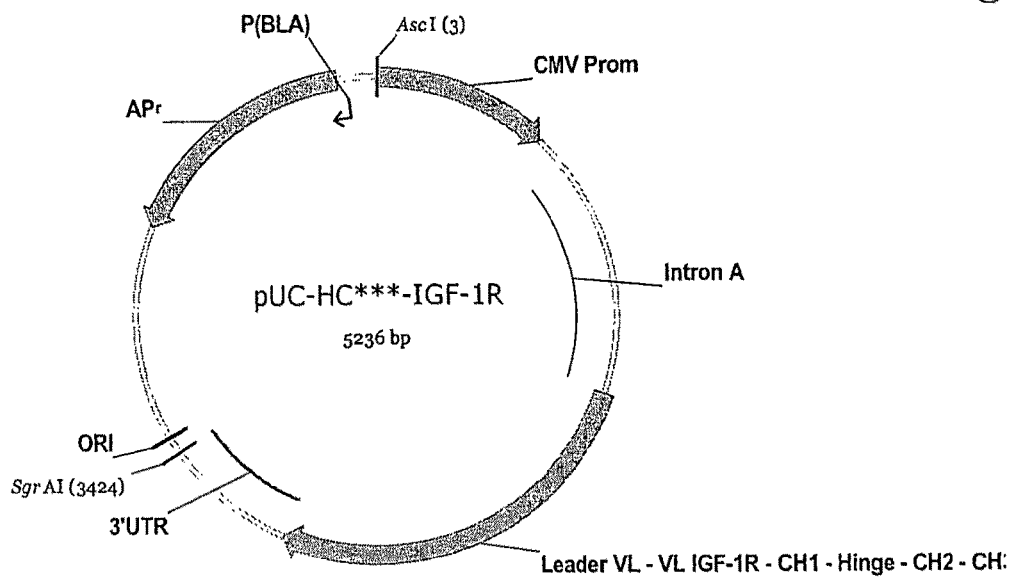
FIG. 7 Plasmid map of heavy chain*<IGF-1R> HC* expression vector pUC-HC*-IGF-1R FIG. 8 Plasmid map of light chain*<IGF-1R> LC* expression vector pUC-LC*-IGF-1R FIG. 9 Plasmid map of the 4700-Hyg-OriP expression vector FIG. 10 Assay principle of cellular FACS IGF-1R-ANGPT2 bridging assay on I24 IGF-1R expressing cells to detect the presence of functional bispecific <ANGPT2-IGF-1R> VL-VH exchange antibody FIG. 11 Scheme IGF-1R ECD Biacore FIG. 12 SDS-PAGE (A) and size exclusion chromatography (B) of purified monospecific, bivalent <IGF-1R> VL-VH exchange antibody (IgG1*) with HC* and LC*** isolated from cell culture supernatants after transient transfection of HEK293-F cells.

The plasmid map of the heavy chain* VL-VH exchange <IGF-1R> HC* expression vector pUC-HC*-IGF-1R is shown in FIG. 7. The amino acid sequence of the <IGF-1R> HC* (including signal sequence) is given in SEQ ID NO: 10.

Vector pUC-LC**-IGF-1R

Vector pUC-LC*-IGF-1R is an expression plasmid e.g. for transient expression of a VL-VH exchange <IGF-1R> light chain LC* (cDNA organized expression cassette; with CMV-Intron A) in HEK293 (EBNA) cells or for stable expression in CHO cells.

Beside the <IGF-1R> LC*** expression cassette this vector contains:

an origin of replication from the vector pUC18 which allows replication of this plasmid in *E. coli*, and a β-lactamase gene which confers ampicillin resistance in *E. coli*.

The transcription unit of the <IGF-1R> LC*** gene is composed of the following elements:

the restriction site Sse8387I at the 5' end the immediate early enhancer and promoter from the human cytomegalovirus, followed by the Intron A sequence, a 5'-untranslated region of a human antibody gene, a immunoglobulin heavy chain signal sequence, the human <IGF-1R> antibody mature LC*** chain encoding a fusion of the human light chain variable domain (VL) and the human γ1-heavy chain constant domains (CH1).

a 3' untranslated region with a polyadenylation signal sequence, and the restriction sites SalI and FseI at the 3'-end.

Figure 8:
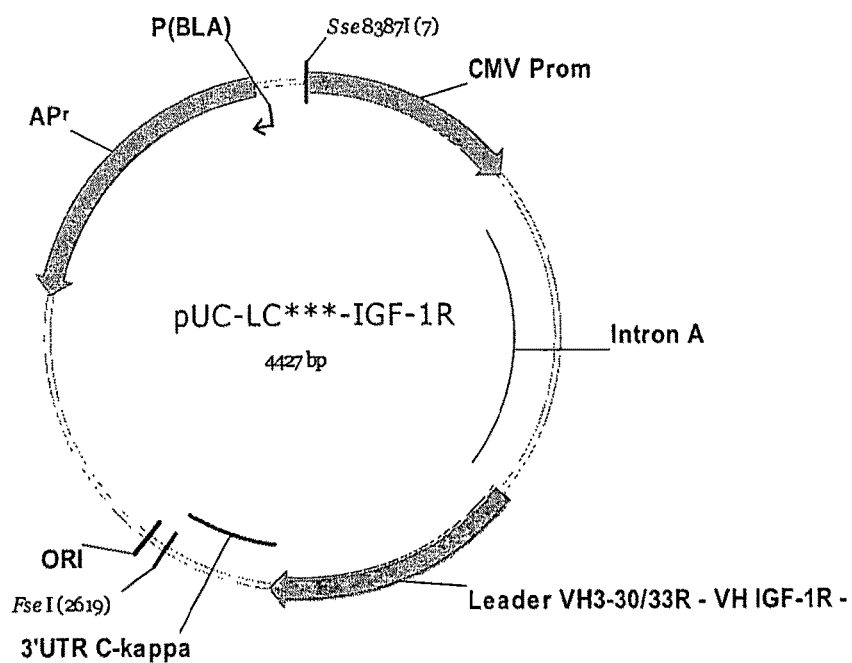

The plasmid map of the light chain* VL-VH exchange <IGF-1R> LC* expression vector pUC-LC*-IGF-1R is shown in FIG. 8. The amino acid sequence of the <IGF-1R> LC* (including signal sequence) is given in SEQ ID NO: 11.

Plasmids pUC-HC*-IGF-1R and pUC-LC*-IGF-1R can be used for transient or stable co-transfections e.g. into HEK293, HEK293 EBNA or CHO cells (2-vector system). For comparative reasons the wildtype <IGF-1R> antibody was transiently expressed from plasmids 4842-pUC-LC-IGF-1R (SEQ ID NO: 2) and 4843-pUC-HC-IGF-1R (SEQ ID NO: 1) analogous to the ones described in this example.

In order to achieve higher expression levels in transient expressions in HEK293 EBNA cells the <IGF-1R> HC* expression cassette can be sub-cloned via AscI, SgrAI sites and the <IGF-1R> LC* expression cassette can be sub-cloned via Sse8387I and FseI sites into the 4700 pUC-Hyg_OriP expression vector containing an OriP element, and a hygromycine resistance gene as a selectable marker.

Figure 9:
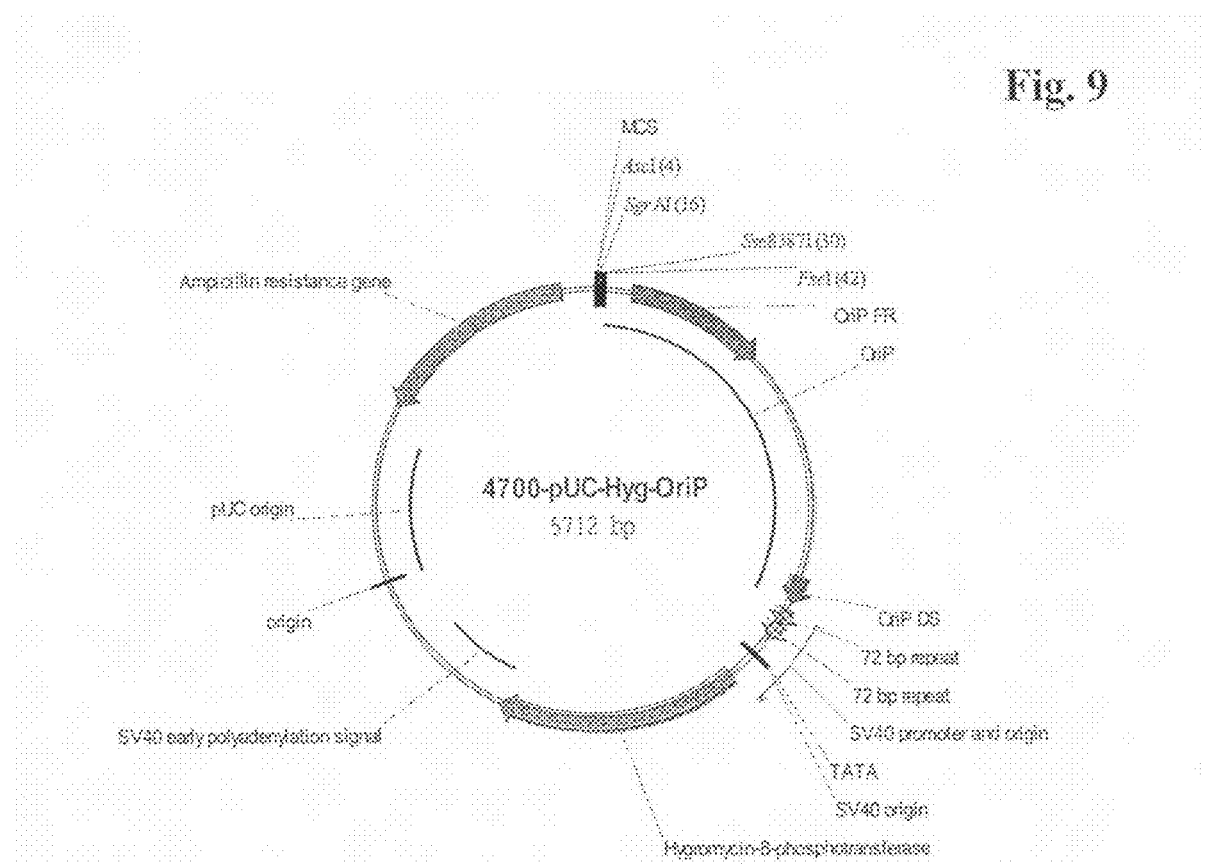

Heavy and light chain transcription units can either be sub-cloned into two independent 4700-pUC-Hyg-OriP vectors for co-transfection (2-vector system) or they can be cloned into one common 4700-pUC-Hyg-OriP vector (1-vector system) for subsequent transient or stable transfections with the resulting vectors. FIG. 9 shows a plasmid map of the basic vector 4700-pUC-OriP.

Example 1B

Making of the Monospecific, Bivalent <IGF-1R> VL-VH Exchange Antibody Expression Plasmids The <IGF-1R> fusion genes (HC* and LC* fusion genes) comprising the exchanged Fab sequences of the wildtype <IGF-1R> antibody were assembled with known recombinant methods and techniques by connection of the according nucleic acid segments.

The nucleic acid sequences encoding the IGF-1R HC* and LC* were each synthesized by chemical synthesis and subsequently cloned into a pPCRScript (Stratagene) based pGA4 cloning vector at Geneart (Regensburg, Germany). The expression cassette encoding the IGF-1R HC*** was ligated into the respective *E. coli* plasmid via PvuII and BmgBI restriction sites resulting in the final vector pUC-HC*-IGF-1R; the expression cassette encoding the respective IGF-1R LC* was ligated into the respective *E. coli* plasmid via PvuII and SalI restriction sites resulting in the final vector pUC-LC***-IGF-1R. The subcloned nucleic acid sequences were verified by DNA sequencing. For transient and stable transfections larger quantities of the plasmids were prepared by plasmid preparation from transformed *E. coli* cultures (Nucleobond AX, Macherey-Nagel)

Example 1C

Transient Expression of Monospecific, Bivalent IGF-1R> VL-VH Exchange Antibody, Purification and Confirmation of Identity by Mass Spectrometry Recombinant <IGF-1R> VL-VH exchange antibody was expressed by transient co-transfection of plasmids pUC-HC*-IGF-1R and pUC-LC*-IGF-1R in HEK293-F suspension cells as described above.

Figure 12B:
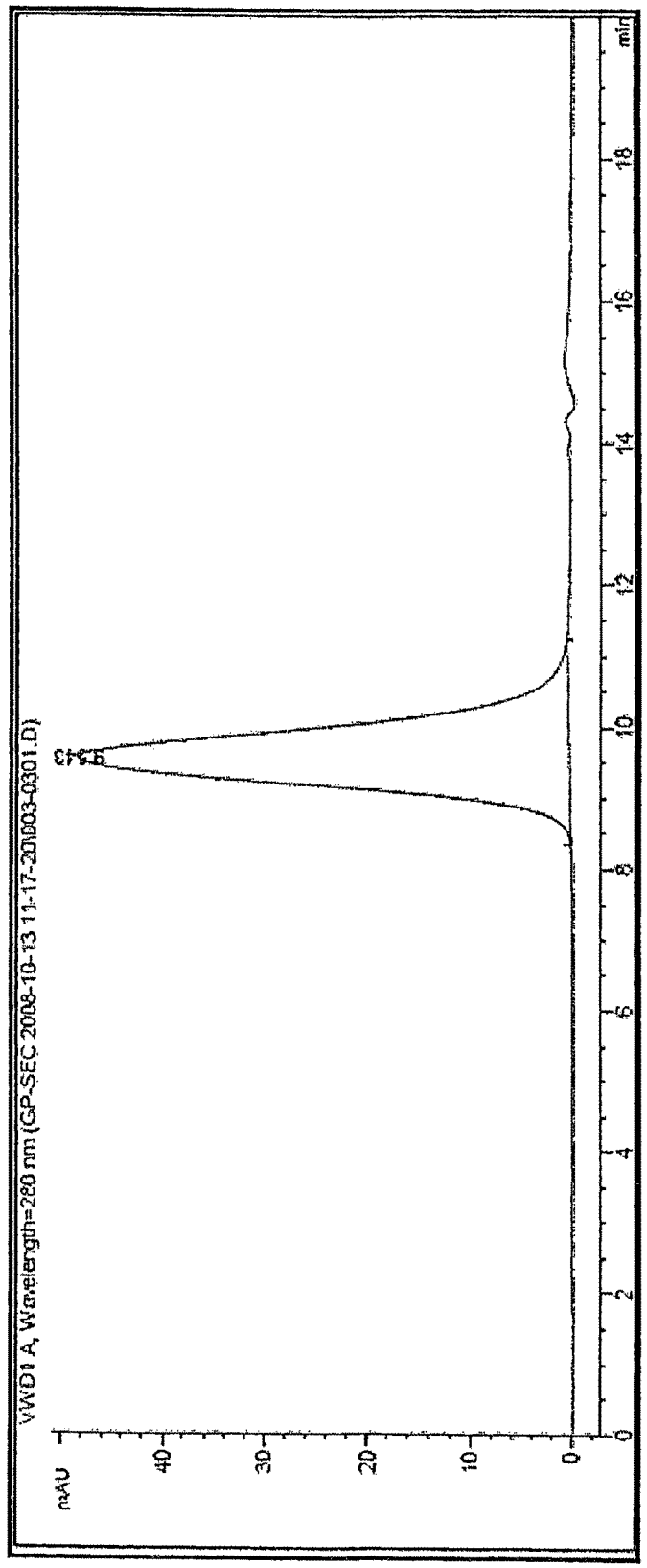

The expressed and secreted monospecific, bivalent <IGF-1R> VL-VH exchange antibody was purified from filtered cell culture supernatants by Protein A affinity chromatography according as described above. In brief, the <IGF-1R> VL-VH exchange antibody containing cell culture supernatants from transient transfections were clarified by centrifugation and filtration and applied to a Protein A HiTrap MabSelect Xtra column (GE Healthcare) equilibrated with PBS buffer (10 mM Na2HPO4, 1 mM KH2PO4, 137 mM NaCl and 2.7 mM KCl, pH 7.4). Unbound proteins were washed out with PBS equilibration buffer followed by 0.1 M sodium citrate buffer, pH 5.5 and washed with PBS. Elution of antibody was achieved with 100 mM sodium citrate, pH 2.8 followed by immediate neutralization of the sample with 300 µl 2 M Tris pH 9.0 per 2 ml fraction. Aggregated protein was separated from monomeric antibodies by size exclusion chromatography on a HiLoad 26/60 Superdex 200 prep grade column (GE Healthcare) in 20 mM Histidine, 150 mM NaCl pH 6.0 and monomeric antibody fractions were subsequently concentrated using a MILLIPORE Amicon Ultra-15 centrifugal concentrator. <IGF-1R> VL-VH exchange antibody was frozen and stored at −20° C. or −80° C. The integrity of the <IGF-1R> VL-VH exchange antibody was analyzed by SDS-PAGE in the presence and absence of a reducing agent and subsequent staining with Coomassie brilliant blue as described above. Monomeric state of the <IGF-1R> VL-VH exchange antibody was confirmed by analytical size exclusion chromatography. (FIG. 12) Characterized samples were provided for subsequent protein analytics and functional characterization. ESI mass spectrometry confirmed the theoretical molecular mass of the completely deglycosylated <IGF-1R> VL-VH exchange antibody.

Example 1D

Figure 13:
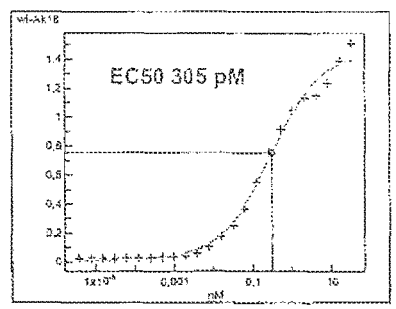
FIG. 13 Binding of monospecific <IGF-1R> VL-VH exchange antibody and wildtype <IGF-1R> antibody to the IGF-1R ECD in an ELISA-based binding assay.
Figure 13:
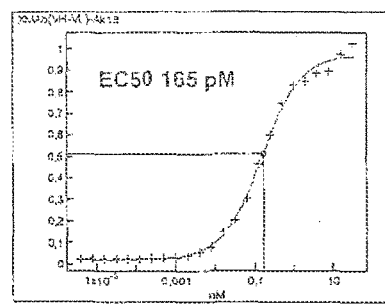

Analysis of the IGF-1R Binding Properties of Monospecific, Bivalent IGF-1R> VL-VH Exchange Antibody in an IGF-1R ECD Binding ELISA and by Biacore The binding properties of monospecific, bivalent <IGF-1R> VL-VH exchange antibody were evaluated in an ELISA assay with the IGF-1R extracellular domain (ECD) as descried above. For this sake the extracellular domain of IGF-1R (residues 1-462) comprising the natural leader sequence and the L1-cysteine rich-12 domains of the human IGF-IR ectodomain of the alpha chain (according to the McKern et al., 1997; Ward et al., 2001) fused to an N-terminal His-Streptavidin binding peptide-tag (His-SBP) was cloned into a pcDNA3 vector derivative and transiently expressed in HEK293F cells. The protein sequence of the IGF-1R-His-SBP ECD is given in see above. The obtained titration curve showed that <IGF-1R> VL-VH exchange antibody was functional and showed comparable binding characteristics and kinetics as the wildtype <IGF-1R> antibody within the error of the method and thus appeared fully functional (FIG. 13).

These findings are being confirmed by Biacore with the respective purified antibodies.

Example 1G

Analysis of the IGF-1R Binding Properties of Monospecific, Bivalent IGF-1R> VL-VH Exchange Antibody by FACS with IGF-1R Over-Expressing I24 Cells In order to confirm the binding activity of <IGF-1R> VL-VH exchange antibody to the IGF-1R over-expressed on the surface of I24 cells (NIH3T3 cells expressing recombinant human IGF-1R, Roche) is studied by FACS. Briefly, 5×10E5 I24 cells per FACS tube are incubated with a dilution of purified <IGF-1R> VL-VH exchange antibody and wildtype <IGF-1R> antibody as a reference and incubated on ice for 1 h. Unbound antibody is washed away with 4 ml ice cold PBS (Gibco)+2% FCS (Gibco). Subsequently, cells are centrifuged (5 min at 400 g) and bound antibody is detected with F(ab')2 <hFcγ>PE conjugate (Dianova) on ice for 1 h protected from light. Unbound detection antibody is washed away with 4 ml ice cold PBS+2% FCS. Subsequently, cells are centrifuged (5 min 400 g), resuspended in 300-500 µL PBS and bound detection antibody is quantified on a FACSCalibur or FACS Canto (BD (FL2 channel, 10.000 cells per acquisition). During the experiment the respective isotype controls are included to exclude any unspecific binding events. Binding of <IGF-1R> VL-VH exchange antibody and wildtype <IGF-1R> reference antibody to IGF-1R on I24 cells result in a comparable, concentration dependent shift of mean fluorescence intensity.

Examples 2

Description of a Monospecific, Bivalent <ANGPT2> Wildtype Antibody

Example 2A

Making of the Expression Plasmids for the Monospecific, Bivalent <ANGPT2> Wildtype Antibody The sequences for the heavy and light chain variable domains of a monospecific, bivalent ANGPT2 <ANGPT2> wildtype antibody including the respective leader sequences described in this example are derived from a human <ANGPT2> antibody heavy chain (SEQ ID NO: 6) and a light chain (SEQ ID NO: 7) described in WO 2006/045049 and the heavy and light chain constant domains are derived from a human antibody (C-kappa and IgG1).

The wildtype <ANGPT2> antibody was cloned into plasmids SB04-pUC-HC-ANGPT2 (SEQ ID NO: 6) and SB06-pUC-LC-ANGPT2 (SEQ ID NO: 7) that are analogous to the vectors described in the previous example 1A.

For comparative reasons and for co-expression experiments (see example 3) the wildtype <ANGPT2> antibody was transiently (co-) expressed from plasmids SB04-pUC-HC-ANGPT2 and SB06-pUC-LC-ANGPT2.

Example 2B

Making of the Monospecific, Bivalent <ANGPT2> Wildtype Antibody Expression Plasmids The nucleic acid sequences encoding the ANGPT2> HC and LC were each synthesized by chemical synthesis and subsequently cloned into a pPCRScript (Stratagene) based pGA4 cloning vector at Geneart (Regensburg, Germany). The expression cassette encoding the <ANGPT2> HC was cloned into the respective E. coli plasmid resulting in the final vector SB04-pUC-HC-ANGPT2; the expression cassette encoding the respective <ANGPT2> LC was cloned into the respective E. coli plasmid resulting in the final vector SB06-pUC-LC-ANGPT2. The subcloned nucleic acid sequences were verified by DNA sequencing. For transient and stable transfections larger quantities of the plasmids were prepared by plasmid preparation from transformed E. coli cultures (Nucleobond AX, Macherey-Nagel).

Examples 3

Expression of Bispecific, Bivalent <ANGPT2-IGF-1R> Antibody, Wherein in the Heavy and Light Chain Specifically Binding to IGF-1R, the Constant Domains VL and VH are Replaced by Each Other (Abbreviated Herein as <ANGPT2-IGF-1R> VL-VH Exchange Antibody)

Example 3A

Transient Co-Expression and Purification of <IGF-1R> VL-VH Exchange Antibody and <ANGPT2> Wildtype Antibody in HEK293 EBNA Cells to Yield Bispecific <ANGPT2-IGF-1R> VL-VH Exchange Antibody In order to generate a functional bispecific antibody recognizing IGF-1R via the <IGF-1R> VL-VH exchange antibody Fab on one side and <ANGPT2> via the <ANGPT2> wildtype Fab region on the other side the two expression plasmids coding for the <IGF-1R> VL-VH exchange antibody (example 1A) were co-expressed with two expression plasmids coding for the <ANGPT2> wildtype antibody. (example 2A). Assuming a statistical association of wildtype heavy chains HC and VL-VH exchange heavy chains HC*** this results in the generation of bispecific and bivalent <IGF-1R-ANGPT2> VL-VH exchange antibody. Under the assumption that both antibodies are equally well expressed and without taking side products into account this should result in a 1:2:1 ratio of the three main products A)<IGF-1R> VL-VH exchange antibody, B) bispecific <IGF-1R-ANGPT2> VL-VH exchange antibody, and C)<ANGPT2> wildtype antibody. Several side products can be expected. However, due to the exchange of only the VL-VH domains the frequency of side products should be reduced compared to the complete Fab crossover. Please note as the <ANGPT2> wildtype antibody showed higher expression transient expression yields than the <IGF-1R> wildtype and <IGF-1R> VL-VH exchange antibodies the ratio of <ANGPT2> wildtype antibody plasmids and <IGF-1R> VL-VH exchange antibody plasmids was shifted in favour of the expression of <ANGPT2> wildtype antibody.

To generate the mix of the main products A)<IGF-1R> VL-VH exchange antibody, B) bispecific <ANGPT2-IGF-1R> VL-VH exchange antibody, and C)<ANGPT2> wildtype antibody the four plasmids pUC-HC*-IGF-1R and pUC-LC*-IGF-1R and plasmids SB04-pUC-HC-ANGPT2 and SB06-pUC-LC-ANGPT2 were transiently co-transfected in suspension HEK293-F cells as described above The harvested supernatant contained a mix of the main products A)<IGF-1R> VL-VH exchange antibody, B) bispecific <ANGPT2-IGF-1R> VL-VH exchange antibody, and C)<ANGPT2> wildtype antibody and is denoted as "Bispecific VL-VH exchange mix". Bispecific VL-VH exchange mix containing cell culture supernatants, were harvested by centrifugation and subsequently purified as described above.

Figure 14:
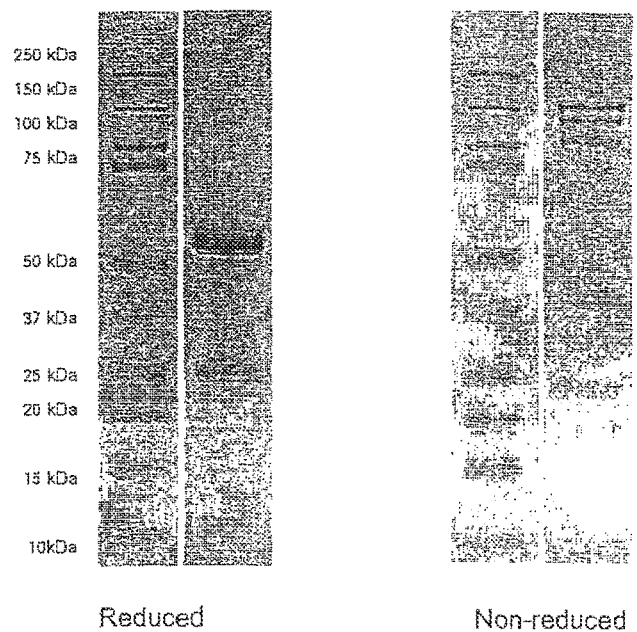
FIG. 14 SDS-PAGE of <ANGPT2-IGF-1R> VL-VH exchange antibody mix purified from cell culture supernatants from transiently transfected HEK293-F SDS-PAGE run under reducing conditions in the left panel and non-reducing conditions in the right panel.

The integrity of the antibody mix was analyzed by SDS-PAGE in the presence and absence of a reducing agent and subsequent staining with Coomassie brilliant blue and by size exclusion chromatography as described. The SDS-PAGE showed that there were 2 different heavy and light chain presents in the preparation as expected (reduced gel) (FIG. 14). Characterized samples were provided for subsequent protein analytics and functional characterization.

Example 3B

Figure 10:
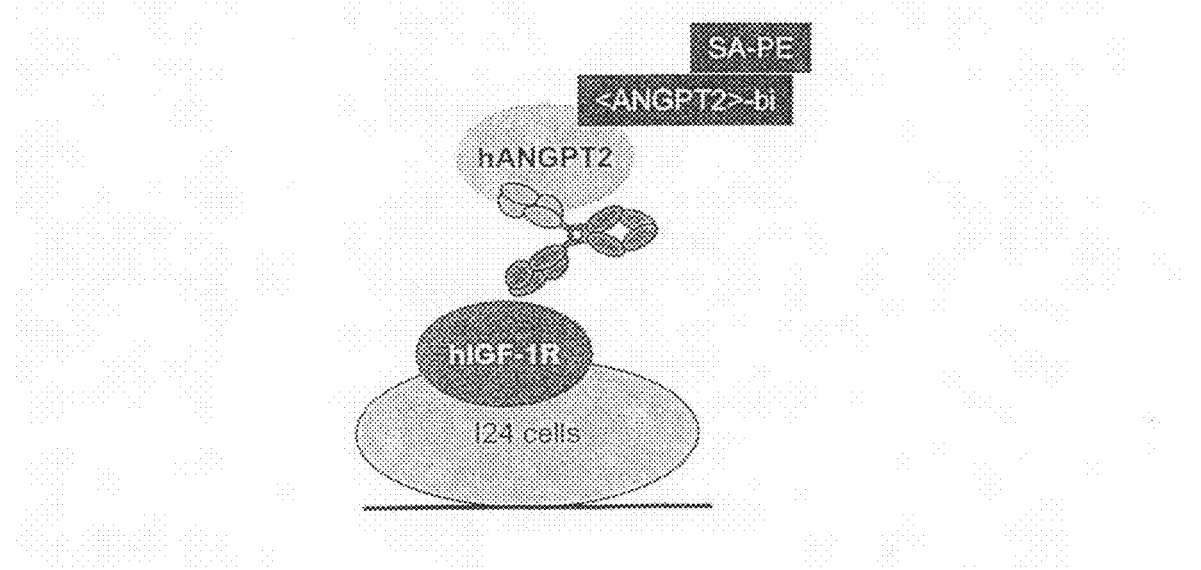

Detection of Functional Bispecific <ANGPT2-IGF-1R> VL-VH Exchange Antibody in a Cellular FACS Bridging Assay on I24 IGF-1R Expressing Cells In order to confirm the presence of functional bispecific <ANGPT2-IGF-1R> VL-VH exchange antibody in the purified bispecific VL-VH exchange mix of the main products A)<IGF-1R> VL-VH exchange antibody, B) bispecific <ANGPT2-IGF-1R> VL-VH exchange antibody, and C)<ANGPT2> wildtype antibody from the transient co-expression described in example 3A, a cellular FACS IGF-1R-ANGPT2 bridging assay on I24 cells (NIH3T3 cells expressing recombinant human IGF-1R, Roche) was performed. The assay principle is depicted in FIG. 10. A bispecific <ANGPT2-IGF-1R> VL-VH exchange antibody that is present in the purified antibody mix is capable of binding to IGF-1R in I24 cells and to ANGPT2 simultaneously; and thus will bridge its two target antigens with the two opposed Fab regions.

Briefly, 5×10E5 I24 cells per FACS tube were incubated with total purified antibody mix and incubated on ice for 1 h (titration 160 µg/ml mix). The respective purified antibodies wildtype <IGF-1R> and <ANGPT2> were applied to the I24 cells as controls. Unbound antibody was washed away with 4 ml ice cold PBS (Gibco)+2% FCS (Gibco), cells were centrifuged (5 min at 400 g) and bound bispecific antibody was detected with 50 µl 2 µg/mL human ANGPT2 (R&D Systems) for 1 h on ice. Subsequently, unbound ANGPT2 was washed away once or twice with 4 ml ice cold PBS (Gibco)+2% FCS (Gibco), cells were centrifuged (5 min at 400 g) and bound ANGPT2 was detected with 50 µl 5 µg/mL <ANGPT2>mIgG1-Biotin antibody (BAM0981, R&D Systems) for 45 min on ice; alternatively, cells were incubated with 50 µl 5 µg/mL mIgG1-Biotin-Isotype control (R&D Systems). Unbound detection antibody was washed away with 4 ml ice cold PBS (Gibco)+2% FCS (Gibco), cells were centrifuged (5 min at 400 g) and bound detection antibody was detected with 50 µl 1:400 Streptavidin-PE conjugate (Invitrogen/Zymed) for 45 min on ice protected from light. Unbound Streptavidin-PE conjugate was washed away with 4 ml ice cold PBS+2% FCS. Subsequently, cells were centrifuged (5 min 400 g), resuspended in 300-500 µL PBS and bound Streptavidin-PE conjugate was quantified on a FACSCalibur (BD (FL2 channel, 10.000 cells per acquisition). During the experiment the respective isotype controls were included to exclude any unspecific binding events. In addition, purified monospecific, bivalent IgG1 antibodies <IGF-1R> and <ANGPT2> were included as controls.

Figure 15:
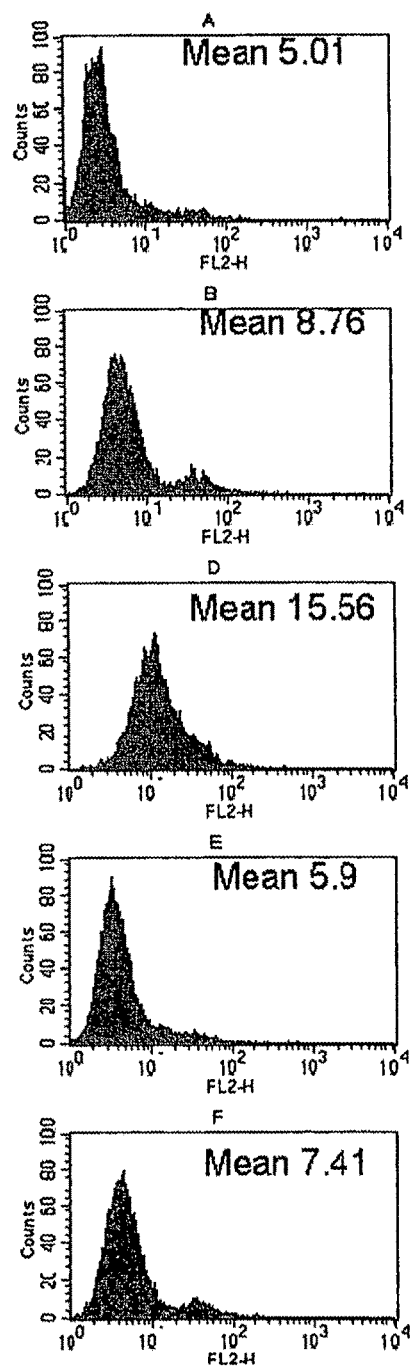
FIG. 15 Results for Samples A to F of cellular FACS IGF-1R-ANGPT2 bridging assay on I24 IGF-1R expressing cells to detect the presence of functional bispecific <ANGPT2-IGF-1R> VL-VH exchange antibody in purified antibody Mix. Purified proteins Sample A to F, from top panel (Sample A) to bottom panel (Sample F)

The results in FIG. 15 show that the incubation with purified antibody crossover mix (<ANGPT2-IGF-1R> VL-VH exchange antibody) from the co-expression of a crossover antibody (<IGF-1R> VL-VH exchange antibody) with a wildtype antibody (<ANGPT2> wildtype antibody) resulted in a significant shift in fluorescence indicating the presence of a functional bispecific <ANGPT2-IGF-1R> VL-VH exchange antibody that was capable of binding to IGF-1R in I24 cells and to ANGPT2 simultaneously; and thus bridges its two target antigens with the two opposed Fab regions. In contrast to this the respective <IGF-1R> and <Ang-2> control antibodies did not result in shift in fluorescence in the FACS bridging assay Taken together these data show that by co-expressing the respective wildtype and crossover plasmids functional bispecific antibodies can be generated. The yields of correct bispecific antibody can be increased by forcing the correct heterodimerization of wildtype and modified crossover heavy chains e.g. using the knobs-into-holes technology as well as disulfide stabilization (see examples 4)

Example 4

Expression of Bivalent, Bispecific <ANGPT2-IGF-1R> VL-VH Exchange Antibody with Modified CH3 Domains (Knobs-into-Holes)

To further improve the yield of the bispecific <ANGPT2-IGF-1R> VL-VH exchange antibody the knobs-into-holes technology is applied to the co-expression of <IGF-1R> VL-VH exchange and wildtype <ANGPT2> antibodies to obtain a homogenous and functional bispecific antibody preparation. For this purpose, the CH3 domain in the heavy chain* HC* of the <IGF-1R> VL-VH exchange antibody is replaced by the CH3 domain (Knobs) of the SEQ ID NO: 8 with a T366W exchange and the CH3 domain in the heavy chain of the wildtype <ANGPT2> antibody is replaced by the CH3 domain (Hole) of the SEQ ID NO: 9 with a T366S, L368A, Y407V exchange or vice versa. In addition, a disulfide can be included to increase the stability and yields as well as additional residues forming ionic bridges and increasing the heterodimerization yields (EP 1870459A1).

The transient co-expression, and the purification of the resulting bivalent, bispecific <ANGPT2-IGF-1R> VL-VH exchange antibody with modified CH3 domains (knobs-into-holes) is performed as described in Example 3.

It should be noted that an optimization of heterodimerization can be achieved e.g. by using different knobs-in-holes technologies such as the introduction of an additional disulfide bridge into the CH3 domain e.g. Y349C into the "knobs chain" and D356C into the "hole chain" and/or combined with the use of residues R409D; K370E (K409D) for knobs residues and D399K; E357K for hole residues described by EP 1870459A1.

Analogously, further bivalent, bispecific VL-VH exchange antibodies with modified CH3 domains (knobs-into-holes) directed against ANGPT2 and another target antigen (using the above described ANGPT2 heavy and light chain and the VL-VH exchange heavy and light chain* HC* and LC* of an antibody directed against said other target, whereby both heavy chains are modified by "knobs-in-holes"), or directed against IGF-1R and another target (using the heavy and light chain of an antibody directed against said other target and the above described IGF-1R VL-VH exchange heavy and light chain* HC* and LC*, whereby both heavy chains are modified by "knobs-in-holes") can be prepared.

The invention claimed is:

1. A bivalent, bispecific antibody comprising two pairs of light chains and heavy chains, each light chain comprising a variable region and a constant region, each heavy chain comprising a variable region and a constant region, wherein:
   a) the light chain and heavy chain of the first of the two pairs specifically bind to a first antigen, wherein the light chain comprises the following domains in N-terminal to C-terminal direction VL, CL and the heavy chain comprises the following domains in N-terminal to C-terminal direction VH, CH1, CH2, CH3; and
   b) the light chain and heavy chain of the second of the two pairs specifically bind to a second antigen, wherein the light chain comprises the following domains in N-terminal to C-terminal direction VH, CL and the heavy chain comprises the following domains in N-terminal to C-terminal direction VL, CH1, CH2, CH3.

2. The bivalent, bispecific antibody of claim 1, wherein the CH3 domain of one heavy chain is altered so that within the interface the CH3 domain of one heavy chain that meets the interface of the CH3 domain of the other heavy chain within the bivalent, bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain, and
   wherein the CH3 domain of the other heavy chain is altered, so that within the interface the CH3 domain of one heavy chain that meets the interface of the CH3 domain of the other heavy chain within the bivalent, bispecific antibody, an amino acid residue is replaced with an amino acid residue having a smaller side chain volume, thereby generating a cavity within the interface of the CH3 domain of the other heavy chain within which a protuberance within the interface of the CH3 domain of the one heavy chain is positionable.

3. The antibody according to claim 2, wherein the amino acid residue having a larger side chain volume is selected from the group consisting of arginine (R), phenylalanine (F), tyrosine (Y), tryptophan (W).

4. The antibody according to claim 2, wherein the amino acid residue having a smaller side chain volume is selected from the group consisting of alanine (A), serine (S), threonine (T), valine (V).

5. The antibody according to claim 2, wherein both CH3 domains are further altered by the introduction of cysteine (C) as amino acid in the corresponding positions of each CH3 domain.

6. The antibody according to claim 3, wherein both CH3 domains are further altered by the introduction of cysteine (C) as amino acid in the corresponding positions of each CH3 domain.

7. The antibody according to claim 4, wherein both CH3 domains are further altered by the introduction of cysteine (C) as amino acid in the corresponding positions of each CH3 domain.

8. A method for the preparation of a bivalent, bispecific antibody according to claim 1 comprising the steps of
   a) transforming a host cell with
      vectors comprising nucleic acid molecules encoding the light chain and heavy chain of the first of the two pairs specifically binding to a first antigen;
      vectors comprising nucleic acid molecules encoding the light chain and heavy chain of the second of the two pairs specifically binding to a second antigen;
   b) culturing the host cell under conditions that allow synthesis of said antibody molecule; and
   c) recovering said antibody molecule from said culture.

9. A composition comprising a bivalent, bispecific antibody according to claim 1 and at least one pharmaceutically acceptable excipient.

10. A composition comprising a bivalent, bispecific antibody according to claim 3 and at least one pharmaceutically acceptable excipient.

11. A composition comprising a bivalent, bispecific antibody according to claim 5 and at least one pharmaceutically acceptable excipient.

12. A composition comprising a bivalent, bispecific antibody according to claim 7 and at least one pharmaceutically acceptable excipient.

* * * * *

SEQUENCE LISTING

<160> NUMBER OF SEQ ID NOS: 12

<210> SEQ ID NO 1
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Phe Gly Leu Ser Trp Val Phe Leu Val Ala Leu Leu Arg Gly
1               5                   10                  15

Val Gln Cys Gln Val Glu Leu Val Glu Ser Gly Gly Gly Val Val Gln
            20                  25                  30

Pro Gly Arg Ser Gln Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Glu Leu Gly Arg Arg Tyr Phe Asp Leu Trp Gly
            115                 120                 125

Arg Gly Thr Leu Val Ser Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
        210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
        450                 455                 460

Pro Gly Lys
465

<210> SEQ ID NO 2
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 2

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Lys Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Lys Trp Pro Pro Trp Thr Phe Gly Gln Gly Thr Lys Val Glu Ser Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
    195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 3
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Lys Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110
```

Lys Trp Pro Pro Trp Thr Phe Gly Gln Gly Thr Lys Val Ser Val Ser
            115                 120                 125

Ser Ala Ser Thr Lys Gly Pro Ser Val Phe Pro Leu Ala Pro Ser Ser
        130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
450                 455

<210> SEQ ID NO 4
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Glu Phe Gly Leu Ser Trp Val Phe Leu Val Ala Leu Leu Arg Gly
1               5                   10                  15

Val Gln Cys Gln Val Glu Leu Val Glu Ser Gly Gly Val Val Gln
            20                  25                  30

Pro Gly Arg Ser Gln Arg Leu Ser Cys Ala Ala Ser Gly Phe Thr Phe
            35                  40                  45

Ser Ser Tyr Gly Met His Trp Val Arg Gln Ala Pro Gly Lys Gly Leu
50                  55                  60

Glu Trp Val Ala Ile Ile Trp Phe Asp Gly Ser Ser Thr Tyr Tyr Ala
65                  70                  75                  80

Asp Ser Val Arg Gly Arg Phe Thr Ile Ser Arg Asp Asn Ser Lys Asn
                85                  90                  95

Thr Leu Tyr Leu Gln Met Asn Ser Leu Arg Ala Glu Thr Ala Val
            100                 105                 110

Tyr Phe Cys Ala Arg Glu Leu Gly Arg Arg Tyr Phe Asp Leu Trp Gly
            115                 120                 125

Arg Gly Thr Leu Val Glu Ser Lys Arg Thr Val Ala Ala Pro Ser Val
130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
            180                 185                 190

Thr Glu Gln Asp Ser Lys Asp Ser Thr Tyr Ser Leu Ser Ser Thr Leu
            195                 200                 205

Thr Leu Ser Lys Ala Asp Tyr Glu Lys His Lys Val Tyr Ala Cys Glu
            210                 215                 220

Val Thr His Gln Gly Leu Ser Ser Pro Val Thr Lys Ser Phe Asn Arg
225                 230                 235                 240

Gly Glu Cys

<210> SEQ ID NO 5
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

```
Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Ala Ala Ala Leu
                485                 490                 495

Glu Val Leu Phe Gln Gly Pro Gly Thr His His His His His His Ser
            500                 505                 510

Gly Asp Glu Lys Thr Thr Gly Trp Arg Gly Gly His Val Val Glu Gly
        515                 520                 525

Leu Ala Gly Glu Leu Glu Gln Leu Arg Ala Arg Leu Glu His His Pro
    530                 535                 540
```

Gln Gly Gln Arg Glu Pro Ser Gly Gly Cys Lys Leu Gly
545                 550                 555

<210> SEQ ID NO 6
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Leu Gly Leu Ser Trp Val Phe Leu Val Ala Ile Leu Glu Gly
1               5                   10                  15

Val Gln Cys Glu Val Gln Leu Val Gln Ser Gly Gly Val Val Gln
            20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Leu Leu Asp Tyr Asp Ile Leu Thr Gly Tyr
        115                 120                 125

Gly Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 7
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

Gly Gln Pro Arg Glu Pro Gln Val Tyr Thr Leu Pro Pro Ser Arg Glu
1               5                   10                  15

Glu Met Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

Gly Gln Pro Arg Glu Pro Gln Val Tyr Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 10
<211> LENGTH: 440
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
        35                  40                  45
Tyr Asp Ala Ser Lys Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Lys Trp Pro Pro
                85                  90                  95
Trp Thr Phe Gly Gln Gly Thr Lys Val Glu Ser Lys Ser Ser Ala Ser
                100                 105                 110
Thr Lys Gly Pro Ser Val Phe Pro Leu Ala Pro Ser Ser Lys Ser Thr
                115                 120                 125
Ser Gly Gly Thr Ala Ala Leu Gly Cys Leu Val Lys Asp Tyr Phe Pro
                130                 135                 140
Glu Pro Val Thr Val Ser Trp Asn Ser Gly Ala Leu Thr Ser Gly Val
145                 150                 155                 160
His Thr Phe Pro Ala Val Leu Gln Ser Ser Gly Leu Tyr Ser Leu Ser
                165                 170                 175
Ser Val Val Thr Val Pro Ser Ser Ser Leu Gly Thr Gln Thr Tyr Ile
                180                 185                 190
Cys Asn Val Asn His Lys Pro Ser Asn Thr Lys Val Asp Lys Lys Val
                195                 200                 205
Glu Pro Lys Ser Cys Asp Lys Thr His Thr Cys Pro Pro Cys Pro Ala
210                 215                 220
Pro Glu Leu Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser His Glu Asp Pro Glu Val Lys Phe Asn Trp Tyr Val
                260                 265                 270
Asp Gly Val Glu Val His Asn Ala Lys Thr Lys Pro Arg Glu Glu Gln
                275                 280                 285
Tyr Asn Ser Thr Tyr Arg Val Val Ser Val Leu Thr Val Leu His Gln
                290                 295                 300
Asp Trp Leu Asn Gly Lys Glu Tyr Lys Cys Lys Val Ser Asn Lys Ala
305                 310                 315                 320
Leu Pro Ala Pro Ile Glu Lys Thr Ile Ser Lys Ala Lys Gly Gln Pro
                325                 330                 335
Arg Glu Pro Gln Val Tyr Thr Leu Pro Pro Ser Arg Asp Glu Leu Thr
                340                 345                 350
Lys Asn Gln Val Ser Leu Thr Cys Leu Val Lys Gly Phe Tyr Pro Ser
                355                 360                 365
Asp Ile Ala Val Glu Trp Glu Ser Asn Gly Gln Pro Glu Asn Asn Tyr
                370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn His Tyr Thr Gln Lys
                420                 425                 430
Ser Leu Ser Leu Ser Pro Gly Lys
                435                 440
```

-continued

```
<210> SEQ ID NO 11
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys
225

<210> SEQ ID NO 12
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Ser Gly Ser Gly Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60
```

```
Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
    370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
    450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Ala Ala Ala Leu
```

-continued

```
                         485                 490                 495
Glu Val Leu Phe Gln Gly Pro Gly Thr His His His His His Ser
            500                 505                 510

Gly Asp Glu Lys Thr Thr Gly Trp Arg Gly Gly His Val Val Glu Gly
        515                 520                 525

Leu Ala Gly Glu Leu Glu Gln Leu Arg Ala Arg Leu Glu His His Pro
    530                 535                 540

Gln Gly Gln Arg Glu Pro Ser Gly Gly Cys Lys Leu Gly
545                 550                 555
```